(12) United States Patent
Zhang et al.

(10) Patent No.: US 8,110,699 B2
(45) Date of Patent: Feb. 7, 2012

(54) COBALT-CATALYZED ASYMMETRIC CYCLOPROPANATION OF ALKENES WITH α-NITRODIAZOACETATES

(75) Inventors: X. Peter Zhang, Tampa, FL (US); Shifa Zhu, Guangzhou (CN)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/559,208

(22) Filed: Sep. 14, 2009

(65) Prior Publication Data

US 2010/0081838 A1 Apr. 1, 2010

Related U.S. Application Data

(60) Provisional application No. 61/096,630, filed on Sep. 12, 2008.

(51) Int. Cl.
C07C 205/00 (2006.01)
C07C 229/00 (2006.01)
(52) U.S. Cl. ............. 560/21; 560/48; 560/124; 530/201
(58) Field of Classification Search .................. 530/201; 560/21, 48, 124
See application file for complete search history.

(56) References Cited

U.S. PATENT DOCUMENTS

| | | | |
|---|---|---|---|
| 6,951,935 | B2 | 10/2005 | Zhang et al. |
| 7,417,140 | B2 | 8/2008 | Pearlman et al. |
| 7,847,041 | B2 | 12/2010 | Zhang |
| 2005/0124596 | A1 | 6/2005 | Zhang et al. |
| 2006/0030718 | A1 | 2/2006 | Zhang et al. |
| 2010/0063277 | A1 | 3/2010 | Zhang et al. |
| 2010/0076239 | A1 | 3/2010 | Zhang |
| 2010/0174104 | A1 | 7/2010 | Zhang et al. |

OTHER PUBLICATIONS

O'Bannon et al., Journal of Organic Chemistry, vol. 54, No. 13, pp. 3096-3101 (1989).*
Penoni et al., European Journal of Inorganic Chemistry, vol. 7, pp. 1452-1460 (2003).*
Adams J. Org. Chem., Diastereoselective Synthesis of Cyclopropane Amino Acids Using Diazo Compounds Generated in Situ, 2003 vol. 68 pp. 9433-9440.
Caselli et al., Inorg. Chim. Acta, 359, 2924, 2006.
Charette Helv. Chim. Acta, Synthesis of α-Nitro-α-diazocarbonyl Derivatives and Their Applications in the Cyclopropanation of Alkenes and in O-H Insertion Reactions, vol. 85 pp. 4468-4484 2002.
Charette A. B., Wurz R. P., J. Mol. Catal. A 2003, 196, 83.
Che et al., J. Am. Chem. Soc. 2001, 123, 4119.
Chen, J. Org. Chem., Asymmetric Cyclopropanation of Styrenes Catalyzed by Metal Complexes of D2-Symmetrical Chiral Porphyrin: Superiority of Cobalt over Iron, vol. 72 pp. 5931-5934, 2007.
Chen et al., J. Am. Chem. Soc. 2004, 126, 14718.
Chen et al., J. Am. Chem. Soc. 2007, 129, 12074.
Davies, Eur. J. Org. Chem., Dirhodium Tetra(N-arylsulfonylprolinates) as Chiral Catalysts for Asymmetric Transformations of Vinyl- and Aryldiazoacetates, pp. 2459-2469, 1999.
Davies et al., J. Am. Chem. Soc. 1996, 118, 6897.
Davies, Org. React., Intermolecular Metal-Catalyzed Carbenoid Cyclopropanations, vol. 57 pp. 1, 2001.
Davies, Chem. Rev., Catalytic Enantioselective C—H Activation by Means of Metal—Carbenoid- Induced C—H Insertion, vol. 103, pp. 2861-2904, 2003.
Deng, J. Am. Chem. Soc., Enantioselective Synthesis of Vinylcyclopropanes and Vinylepoxides Mediated by Camphor-Derived SulfurYlides: Rationale of Enantioselectivity, Scope, and Limitation, vol. 128 pp. 9730-9740, 2006.
Doyle, Chem. Rev., Catalytic methods for metal carbene transformations, vol. 86 pp. 919-939, 1986.
Doyle, Org. Lett., Dirhodium(II) Tetrakis[methyl 2-oxaazetidine-4-carboxylate]: A Chiral Dirhodium(II) Carboxamidate of Exceptional Reactivity and Selectivity, vol. 2 pp. 1145-1147, 2000.
Doyle et al., J. Am. Chem. Soc., 115, 9968, 1993.
Du, Organometallics, Asymmetric Cyclopropanation of Styrene Catalyzed by Chiral Macrocyclic Iron(II) Complexes, vol. 21 pp. 4490, 2002.
Evans et al., J. Am. Chem. Soc., 113, 726, 1991.
Fritschi et al., Angew. Chem., Int. Ed. Engl., 25, 1005, 1986.
Haener, Chimia, Nitration of the DBHA Cyclopropanecarboxylate Enolate—A New and Efficient Route to 1- Aminocyclopropane-1-carboxylic Acid, vol. 39 pp. 356-357, 1985.
Hu, Org. Lett., In search of high stereocontrol for the construction of cis-disubstituted cyclopropane compounds. Total synthesis of a cyclopropane-configured urea- PETT analogue that is a HIV-1 reverse transcriptase inhibitor, vol. 4 pp. 901, 2002.
Huang, J. Org. Chem. Diastereoselective and Enantioselective Cyclopropanation of Alkenes Catalyzed by Cobalt Porphyrins, vol. 68 pp. 8179-8184, 2003.
Ikeno, Bull. Chem. Soc. Jpn, Highly Enantioselective Cyclopropanation of Styrenes and Diazoacetates Catalyzed by 3-Oxobutylideneaminatocobalt(II) Complexes, Part 1. Designs of Cobalt Complex Catalysts and the Effects of Donating Ligands, vol. 74, pp. 2139-2150, 2001.
Kunz, J. Am. Chem. Soc., Enantioselective Organocatalytic Cyclopropanations. The Identification of a New Class of Iminium Catalyst Based upon Directed Electrostatic Activation, vol. 127 pp. 3240-3241, 2005.
Lasa, Synlett, Synthesis of Enantiomerically Pure 1-Amino-2-phenylcycloalkanecarboxylic Acids (cnPhe), pp. 2517, 2006.
Lo, M. M.-C., Fu G. C., J. Am. Chem. Soc., 120, 10270, 1998.
Lou, J. Am. Chem. Soc., A New Chiral Rh(II) Catalyst for Enantioselective [2 + 1]-Cycloaddition. Mechanistic Implications and Applications, vol. 126 pp. 8916-8918, 2004.
Miller et al., Agnew. Chem., Int. Ed. Engl., 41, 2953, 2002.
Moreau, J. Am. Chem. Soc., Expedient Synthesis of Cyclopropane α-Amino Acids by the Catalytic Asymmetric Cyclopropanation of Alkenes Using Iodonium Ylides Derived from Methyl Nitroacetate, vol. 127 pp. 18014-18015, 2005.

(Continued)

*Primary Examiner* — Porfirio Nazario Gonzalez
(74) *Attorney, Agent, or Firm* — Bryan Cave LLP

(57) ABSTRACT

A process for the cyclopropanation of olefins with a metal porphyrin catalyst and an acceptor/acceptor substituted diazo reagent.

30 Claims, No Drawings

OTHER PUBLICATIONS

Muller, Tetrahedron, Rh(II)-Catalyzed asymmetric carbene transfer with ethyl 3,3,3-trifluoro-2- diazopropionate, vol. 60 pp. 4755-4763, 2004.

Nakamura et al., J. Am. Chem. Soc. 100, 3443, 1978.

Niimi et al., Adv. Synth. Catal. 343, 79; Fe-catalyzed systems, 2001.

Nishiyama et al., J. Am. Chem. Soc., 116, 2223, 1994.

O'bannon, J. Org. Chem., Catalytic cyclopropanation of alkenes with ethyl nitrodiazoacetate. A facile synthesis of ethyl 1-nitrocyclopropanecarboxylates, vol. 54 pp. 3096-3101, 1989.

Papageorgiou et al., Angew. Chem., 115, 852; Angew. Chem. Int. Ed. 2003, 42, 828, 2003.

Wurz, Org. Lett., Hypervalent Iodine(III) Reagents as Safe Alternatives to α-Nitro-α- diazocarbonyls, vol. 5, pp. 2327-2329, 2003.

Wurz, Org. Lett., Doubly Activated Cyclopropanes as Synthetic Precursors for the Preparation of 4-Nitro- and 4-Cyano-dihydropyrroles and Pyrroles, vol. 7 pp. 2313-2316, 2005.

Wurz R. P., Charette A. B., J. Org. Chem., 69, 1262, 2004.

Wurz, "The Development of an Expedient Method for the Synthesis of a Diverse Series of Cyclopropane alpha-Amino Acids", Thesis presented to University of Montreal 2004.

Yashin, et al., Tetrahedron Letters, 44, 8241-8244, 2003.

Yashin, Synthesis, Reduction of 1-Nitrospiro[2.2]pentanecarboxylates: Convenient Synthesis of Novel Polyspirocyclic Cyclopropane Amino Acids, pp. 279-284, 2006.

Zhu et al., J. Am. Chem. Soc. 130, 5042, 2008.

Dzik, Wojciech I; Xu, Xue; Zhang, Peter X.; Reek, Joost N. H.; and Bruin, Bas De, Carbene Radicals' in CoII(por)-Catalyzed Olefin Cyclopropanation, J. Am. Chem. Soc., May 3, 2010, 10891-10902, 132, doi 10.1021/ ja103768r.

Lu, Hongjian;Dzik, Wojciech I.; Xu, Xue; Wojtas, Lukasz; Bruin, Bas De; Zhang, Peter X., Experimental Evidence for Cobalt(III)-Carbene Radicals: Key Intermediates in Cobalt(II)-Based Metalloradical Cyclopropanation, J. Am. Chem. Soc., May 12, 2011, 8518-8521, 133(22), doi 10.1021/ja203434c.

* cited by examiner

COBALT-CATALYZED ASYMMETRIC CYCLOPROPANATION OF ALKENES WITH α-NITRODIAZOACETATES

CROSS-REFERENCE TO RELATED APPLICATIONS

The present application claims the benefit of U.S. Provisional Application Ser. No. 61/096,630, filed Sep. 12, 2008, which is hereby incorporated by reference herein in its entirety.

STATEMENT OF GOVERNMENT RIGHTS

This invention was made with Government support under grant number NSF 0711024 awarded by the National Science Foundation. The government has certain rights in the invention.

FIELD OF THE INVENTION

The present invention generally relates to metal-catalyzed cyclopropanation of olefins. More particularly, the present invention relates to a process for asymmetric cyclopropanation of olefins using α-nitrodiazoacetate as a reagent.

BACKGROUND OF THE INVENTION

Cyclopropanes are an important class of compounds that have found numerous fundamental and practical applications. (Pietruszka J., Chem. Rev. 2003, 103, 1051; Wessjohann et al., Chem. Rev. 2003, 103, 1625; Donaldson W. A., Tetrahedron 2001, 57, 8589; Salaun J., Chem. Rev. 1989, 89, 1247.) One of the most general approaches for stereoselective construction of cyclopropanes, which are the smallest all-carbon cyclic molecules, is the metal-catalyzed asymmetric cyclopropanation of alkenes with diazo reagents. (Lebel et al., Chem. Rev. 2003, 103, 977; Davies H. M. L., Antoulinakis E., Org. React. 2001, 57, 1; Doyle M. P., Forbes D. C., Chem. Rev. 1998, 98, 911; Padwa A., Krumpe K. E., Tetrahedron 1992, 48, 5385; Doyle M. P., Chem. Rev. 1986, 86, 919.) Among the three classes of common diazo reagents, (Davies H. M. L., Beckwith R. E. J., Chem. Rev. 2003, 103, 2861) acceptor-substituted diazo reagents, such as diazoesters, are well-established as the most effective carbene sources for metal-catalyzed stereoselective cyclopropanation. (For selected examples of asymmetric cyclopropanation with diazocarbonyls, see: Cu-catalyzed systems: Fritschi et al., Agnew. Chem., Int. Ed. Engl. 1986, 25, 1005; Fristchi et al., Angew. Chem. 1986, 98, 1028; Evans et al., J. Am. Chem. Soc. 1991, 113, 726; Lo M. M.-C., Fu G. C., J. Am. Chem. Soc. 1998, 120, 10270; R-catalyzed systems: Doyle et al., J. Am. Chem. Soc. 1993, 115, 9968; Hu et al., Org. Lett. 2002, 4, 901; Lou et al., J. Am. Chem. Soc. 2004, 126, 8916; Ru-catalyzed systems: Nishiyama et al., J. Am. Chem. Soc. 1994, 116, 2223; Che et al., J. Am. Chem. Soc. 2001, 123, 4119; Miller et al., Agnew. Chem., Int. Ed. Engl. 2002, 41, 2953; Co-catalyzed systems: Nakamura et al., J. Am. Chem. Soc. 1978, 100, 3443; (keno et al., Bull. Chem. Soc. Jpn. 2001, 74, 2139; Niimi et al., Adv. Synth. Catal. 2001, 343, 79; Fe-catalyzed systems: Du et al., Organometallics 2002, 21, 4490.)

There has been great progress in metal-catalyzed selective carbene transfers with donor/acceptor-substituted diazo reagents such as vinyldiazoesters and aryldiazoesters. (Davies et al., J. Am. Chem. Soc. 1996, 118, 6897; Davies H. M. L., Eur. J. Org. Chem. 1999, 2459.) However, asymmetric cyclopropanation with acceptor/acceptor-substituted diazo reagents remains a major challenge in the field because of their inherent low reactivity and perceived poor enantioselectivity. Therefore, more reactive and enantiodiscriminating catalysts need to be developed to meet this challenge.

A family of cobalt(II) $D_2$-symmetric chiral porphyrins [Co(Por)] with tunable electronic, steric, and chiral environments (Formulae A-F), has emerged as a new class of effective catalysts for various asymmetric cyclopropanation reactions, including that of electron-deficient olefins with diazosulfones. (Huang et al., J. Org. Chem. 2003, 68, 8179; Chen et al., J. Am. Chem. Soc. 2004, 126, 14718; Chen Y., Zhang X. P., J. Org. Chem. 2007, 72, 5931; Chen et al., J. Am. Chem. Soc. 2007, 129, 12074; Zhu et al., J. Am. Chem. Soc. 2008, 130, 5042. For other contributions on [Co(Por)]-catalyzed cyclopropanation, see: Penoni et al., Eur. J. Inorg. Chem. 2003, 1452; Caselli et al., Inorg. Chim. Acta 2006, 359, 2924.) Having recognized their distinct catalytic properties, we initiated a project to examine the potential of $Co^{II}$-based catalysts for asymmetric cyclopropanation with acceptor/acceptor-substituted diazo reagents. Our first target was α-nitro-diazoacetates (NDAs) as the resulting cyclopropanes have been demonstrated to be valuable precursors for a number of useful compounds, including the synthetically and biologically important cyclopropane α-amino acids and aminocyclopropanes (Reaction Schemes H and J). (In addition to the wide substrate scope and high selectivity (both diastereo- and enantioselectivity), the $Co^{II}$-based catalytic system enjoys a practical attribute that is atypical for metal-catalyzed carbene transfer—it can be operated in a one-pot fashion with alkenes as limiting reagents and requires no slow addition of diazo reagents.) (As reported in O'Bannon et al., J. Org. Chem. 1989 and O'Bannon et al., Tetrahedron 1990, α-nitrodiazoacetates were synthesized on multigram scales and were found to be stable for long storage periods without observation of decomposition or experience of explosion. In general, however, diazo reagents may be explosive and should be handled with great care.) (Haener R., Seebach D., Chimia 1985, 39, 356; Yashin et al., Tetrahedron Lett. 2003, 44, 8241; Wurz R. P., Charette A. B., J. Org. Chem. 2004, 69, 1262; Wurz R. P., Charette A. B., Org. Lett. 2005, 7, 2313; Yashin et al., Synthesis 2006, 279; Lasa M., Cativiela C., Synlett 2006, 2517.) Among several previous efforts toward metal-catalyzed cyclopropanation with NDA, it is notable that Charette et al. conducted a systematic evaluation of the reaction by employing various Rh- and Cu-based chiral catalysts. (O'Bannon P. E., Dailey W. D., J. Org. Chem. 1989, 54, 3096; O'Bannon P. E., Dailey W. D., Tetrahedron 1990, 46, 7341; Charette et al., Helv. Chim. Acta 2002, 85, 4468; Charette A. B., Wurz R. P., J. Mol. Catal. A 2003, 196, 83.) (For selected examples of the use of other acceptor/acceptor-substituted diazo reagents for asymmetric cyclopropanation, see: Doyle et al., Org. Lett. 2000, 2, 1145; Muller et al., Tetrahedron 2004, 60, 4755.) While the desired cyclopropanes were obtained predominantly as E isomers in good yields, the best enantioselectivity, which was achieved by using a Cu-based catalyst in the presence of ethyl diazoacetate (20%) as additive, was 72% ee. (For an alternative approach of using iodonium ylides to achieve high diastereo- and enantioselectivity, see: Wurz R. P., Charette A. B., Org. Lett. 2003, 5, 2327; Moreau B., Charette A. B., J. Am. Chem. Soc. 2005, 127, 18014.)

We report herein a $Co^{II}$-based catalytic system for highly diastereo- and enantioselective cyclopropanation of various alkenes with NDA. (For selected examples of other catalytic asymmetric cyclopropanation reactions that generate highly substituted cyclopropanes, see: Papageorgiou et al., Angew. Chem. 2003, 115, 852; Angew. Chem. Int. Ed. 2003, 42, 828; Adams et al., J. Org. Chem. 2003, 68, 9433; Kunz et al., J. Am. Chem. Soc. 2005, 127, 3240; Deng et al., J. Am. Chem. Soc. 2006, 128, 9730.) Furthermore, the catalytic process provided the atypical Z isomers as the dominant products.

SUMMARY OF THE INVENTION

Among the various aspects of the present invention is the provision of a process for metal-porphyrin catalyzed asymmetric cyclopropanation of olefins with an α-nitro diazo reagent.

Briefly, therefore, the present invention is directed to a process for metal-porphyrin catalyzed asymmetric cyclopropanation of olefins wherein the process generally corresponds to the following reaction scheme:

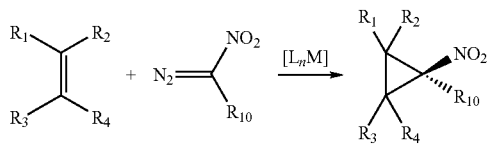

wherein [$L_nM$] is a metal porphyrin complex; $R_1$, $R_2$, $R_3$ and $R_4$ are independently hydrogen, hydrocarbyl, substituted hydrocarbyl, heterocyclo, or an electron withdrawing group; and $R_{10}$ is an electron acceptor.

The present invention is further directed to a process for metal-porphyrin catalyzed asymmetric cyclopropanation of olefins wherein the process generally corresponds to the following reaction scheme:

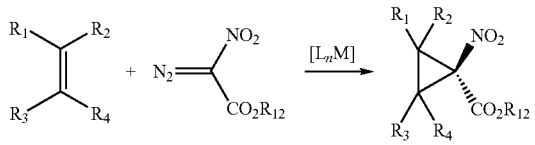

wherein [$L_nM$] is a metal porphyrin complex; $R_1$, $R_2$, $R_3$ and $R_4$ are independently hydrogen, hydrocarbyl, substituted hydrocarbyl, heterocyclo, or an electron withdrawing group; and $R_{12}$ is hydrogen, hydrocarbyl, substituted hydrocarbyl, or heterocyclo.

Another aspect of the invention is the further reaction of the cyclopropanation products into the synthetically and biologically important cyclopropane α-amino acids or aminocyclopropanes, wherein the process generally corresponds to the following reaction scheme:

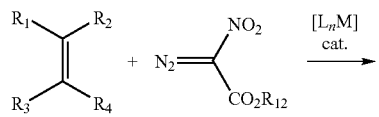

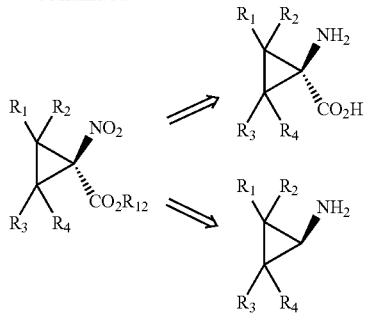

wherein [$L_nM$] is a metal porphyrin complex; $R_1$, $R_2$, $R_3$ and $R_4$ are independently hydrogen, hydrocarbyl, substituted hydrocarbyl, heterocyclo, or an electron withdrawing group; and $R_{12}$ is hydrogen, hydrocarbyl, substituted hydrocarbyl, or heterocyclo.

Other objects and features will be in part apparent and in part pointed out hereinafter.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$— or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The terms "alkoxy" or "alkoxyl" as used herein alone or as part of another group denote any univalent radical, RO— where R is an alkyl group.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl, and the like. The substituted alkyl groups described herein may have, as substituents, any of the substituents identified as substituted hydrocarbyl substituents.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The substituted aryl groups described herein may have, as substituents, any of the substituents identified as substituted hydrocarbyl substituents.

The terms "diazo" or "azo" as used herein alone or as part of another group denote an organic compound with two linked nitrogen compounds. These moieties include without limitation diazomethane, ethyl diazoacetate, and t-butyl diazoacetate.

The term "electron acceptor" as used herein denotes a chemical moiety that accepts electrons. Stated differently, an electron acceptor is a chemical moiety that accepts either a fractional electronic charge from an electron donor moiety to form a charge transfer complex, accepts one electron from an electron donor moiety in a reduction-oxidation reaction, or accepts a paired set of electrons from an electron donor moiety to form a covalent bond with the electron donor moiety.

The terms "halogen" or "halo" as used herein alone or as part of another group denote chlorine, bromine, fluorine, and iodine.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxyl, protected hydroxyl, acyl, acyloxy, alkoxy, alkenoxy, alkynoxyl, aryloxy, halogen, amido, amino, nitro, cyano, thiol, ketals, acetals, esters and ethers.

The term "heteroatom" as used herein denotes atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remaded of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxyl, protected hydroxyl, acyl, acyloxy, alkoxy, alkenoxy, alkynoxyl, aryloxy, halogen, amido, amino, nitro, cyano, thiol, ketals, acetals, esters and ethers.

The terms "hydrocarbon" and "hydrocarbyl" as used herein alone or as part of another group denote organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl, and alkynaryl. Unless otherwise indicated, these moieties preferably comprise 1 to 20 carbon atoms.

The term "porphyrin" as used herein denotes a compound comprising a fundamental skeleton of four pyrrole nuclei united through the α-positions by four methane groups to form the following macrocyclic structure:

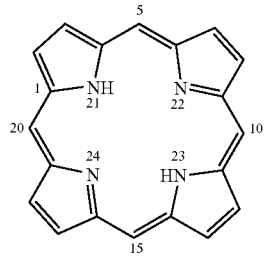

The term "substituted hydrocarbyl" as used herein alone or as part of another group denotes hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substitutents include halogen, heterocyclo, alkoxy, alkenoxy, alkynoxyl, aryloxy, hydroxyl, protected hydroxy, keto, acyl, acyloxy, nitro, amino, amido, nitro, cyano, thiol, ketals, acetals, esters and ethers.

The term "tpp" as used herein denotes the moiety tetraphenyl porphyrin.

DETAILED DESCRIPTION OF THE INVENTION

In accordance with the process of the present invention, compounds containing an ethylenic bond, commonly known as olefins, are cyclopropanated with a diazo reagent in the presence of a metal porphyrin complex. Advantageously, the metal porphyrin catalyzed process proceeds relatively efficiently under relatively mild and neutral conditions, in a one-pot fashion, with olefins as limiting reagents and without the need for slow-addition of diazo reagents.

In general, the olefin may be any of a wide range of olefins. In typical embodiments, the olefin is selected from the group consisting of aromatic olefins, non-aromatic olefins, di-substituted olefins, tri-substituted olefins, tetra-substituted olefins, cis-olefins, trans-olefins, cyclic olefins, and non-cyclic olefins. In one preferred embodiment, the olefin corresponds to the following Formula X:

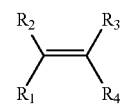

Formula X wherein $R_1$, $R_2$, $R_3$, and $R_4$ are independently hydrogen, hydrocarbyl, substituted hydrocarbyl, heterocyclo, or electron withdrawing group. For cyclic alkenes, two of $R_1$, $R_2$, $R_3$, and $R_4$, in combination with the atoms of the olefin to which they are attached, define a ring. In one embodiment where the olefin corresponds to Formula X, $R_1$, $R_2$, $R_3$, and $R_4$ are independently hydrogen, alkyl, alkenyl, alkynyl, or aryl. In another embodiment, at least one of $R_1$, $R_2$, $R_3$, and $R_4$ is heterosubstituted and the remainder are independently hydrogen, alkyl, alkenyl, alkynyl, or aryl. In one preferred embodiment in which the olefin corresponds to Formula X, the olefin is an α,β-unsaturated olefin. For example, the olefin may be an α,β-unsaturated olefin, an α,β-unsaturated ester, or an α,β-unsaturated ketoolefin. In a preferred embodiment, the olefin is an α,β-unsaturated olefin corresponding to the following Formula Y:

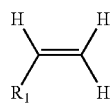

Formula Y wherein $R_1$ is optionally substituted alkyl, optionally substituted alkenyl, optionally substituted alkynyl, or optionally substituted aryl. In one particularly preferred embodiment where the olefin corresponds to Formula Y, $R_1$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^a R^b$ where $R^a$ and $R^b$ are independently hydrogen, hydrocarbyl, substituted hydrocarbyl or heterocyclo.

In a typical embodiment, the olefin corresponds to Formula 1:

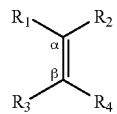

Formula 1 wherein $R_1$ and $R_2$ are substituents of the α-carbon of the ethylenic bond; $R_3$ and $R_4$ are substituents of the β-carbon of the ethylenic bond; and $R_1$, $R_2$, $R_3$, and $R_4$ are independently hydrogen, hydrocarbyl, substituted hydrocarbyl, heterocyclo, or an electron withdrawing group.

In certain preferred embodiments, the olefin corresponds to Formula 1. In one such preferred embodiment, $R_1$ is hydrogen. In another preferred embodiment, $R_1$ is alkyl or substituted alkyl. In a further preferred embodiment, $R_1$ is aryl, typically phenyl or substituted phenyl. In one embodiment, $R_2$ is hydrogen. In another embodiment, $R_2$ is alkyl or substituted alkyl. In a preferred embodiment, $R_2$ is aryl, typically phenyl or substituted phenyl. In one embodiment, $R_3$ is hydrogen. In another embodiment, $R_3$ is alkyl or substituted alkyl. In a preferred embodiment, $R_3$ is aryl, typically phenyl or substituted phenyl. In one embodiment, $R_4$ is hydrogen. In another embodiment, $R_4$ is alkyl or substituted alkyl. In a preferred embodiment, $R_4$ is aryl, typically phenyl or substituted phenyl. In an embodiment, two of $R_1$, $R_2$, $R_3$ and $R_4$ are hydrogen. In an alternate embodiment, three of $R_1$, $R_2$, $R_3$, and $R_4$ are hydrogen. In another alternate embodiment, $R_3$ and $R_4$ are both hydrogen. In a different embodiment, $R_1$, $R_2$ and the α-carbon, or $R_3$, $R_4$ and the β-carbon form a carbocyclic or heterocyclic ring. In an additional embodiment, $R_1$, $R_3$, the α-carbon, and the β-carbon or $R_2$, $R_4$, the α-carbon, and the β-carbon form a carbocyclic or heterocyclic ring. In yet another embodiment, $R_1$, $R_4$, the α-carbon, and the β-carbon or $R_2$, $R_3$, the α-carbon, and the β-carbon form a carbocyclic or heterocyclic ring. In one preferred embodiment, one of $R_1$, $R_2$, $R_3$, and $R_4$ is an electron withdrawing group. In another, alternative preferred embodiment, at least one of $R_1$, $R_2$, $R_3$, and $R_4$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^a R^b$ where $R^a$ and $R^b$ are independently hydrogen, hydrocarbyl, substituted hydrocarbyl or heterocyclo. In a further preferred embodiment, at least one of $R_1$, $R_2$, $R_3$ and $R_4$ is —C(O)CH$_3$, —C(O)OCH$_3$, —C(O)OC$_2$H$_5$, or —C(O)N$R^a R^b$, where $R^a$ and $R^b$ are independently alkyl. In a still further preferred embodiment, at least one of $R_1$, $R_2$, $R_3$ and $R_4$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl. In certain preferred embodiments, the olefin of Formula 1 is an aromatic olefin, an α,β-unsaturated ester, or an α,β-unsaturated ketone.

In an embodiment where the olefin corresponds to Formula 1 and one, but only one of $R_1$, $R_2$, $R_3$, and $R_4$ is an electron withdrawing group, e.g., $R_2$ is an electron withdrawing group, the olefin corresponds to Formula 1-EWG:

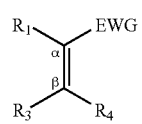

Formula 1-EWG wherein $R_1$ and EWG are substituents of the α-carbon of the ethylenic bond; $R_3$ and $R_4$ are substituents of the β-carbon of the ethylenic bond; $R_1$, $R_3$, and $R_4$ are independently hydrogen, hydrocarbyl, substituted hydrocarbyl, heterocyclo, or an electron withdrawing group; and EWG is an electron withdrawing group. For example, in one preferred embodiment where the olefin corresponds to Formula 1-EWG, $R_1$, $R_3$ and $R_4$ may be any of the moieties identified as preferred or alternative embodiments for $R_1$, $R_3$ and $R_4$ in connection with Formula 1. In a particularly preferred embodiment, $R_1$, $R_3$ and $R_4$ are hydrogen.

In one preferred embodiment, the olefin corresponds to Formula 1 and one but only one of $R_1$, $R_2$, $R_3$, and $R_4$ is hydrogen. In an example of this embodiment, $R_2$ is hydrogen, and the olefin corresponds to Formula 2:

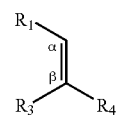

Formula 2 wherein $R_1$ is a substituent of the α-carbon of the ethylenic bond; $R_3$ and $R_4$ are substituents of the β-carbon of the ethylenic bond; and $R_1$, $R_3$, and $R_4$ are independently hydrogen, hydrocarbyl, substituted hydrocarbyl, heterocyclo, or an electron withdrawing group. For example, in one preferred embodiment where the olefin corresponds to Formula 2, $R_1$, $R_3$ and $R_4$ may be any of the moieties identified as preferred or alternative embodiments for $R_1$, $R_3$ and $R_4$ in connection with Formula 1.

In particularly preferred embodiments where the olefin corresponds to Formula 2, at least one of $R_1$, $R_3$, and $R_4$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^a R^b$ where $R^a$ and $R^b$ are independently hydrogen, hydrocarbyl, substituted hydrocarbyl or heterocyclo. In an even more preferred embodiment where the olefin corresponds to Formula 2, at least one of $R_1$, $R_3$ and $R_4$ is —C(O)CH$_3$, —C(O)OCH$_3$, —C(O)OC$_2$H$_5$, or —C(O)N$R^a R^b$, where $R^a$ and $R^b$ are independently alkyl. In a still further preferred embodiment where the olefin corresponds to Formula 2, at least one of $R_1$, $R_3$ and $R_4$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl.

In one embodiment where the olefin corresponds to Formula 2, $R_1$, $R_3$, or $R_4$ may be an electron withdrawing group. In an example of this embodiment, the substituent on the α-carbon, i.e., $R_1$, is an electron withdrawing group, and the olefin corresponds to Formula 2-EWG(a):

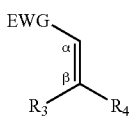

Formula 2-EWG(a)

wherein EWG is a substituent of the α-carbon of the ethylenic bond; $R_3$ and $R_4$ are substituents of the β-carbon of the ethylenic bond; $R_3$ and $R_4$ are independently hydrogen, hydrocarbyl, substituted hydrocarbyl, heterocyclo, or an electron withdrawing group; and EWG is an electron withdrawing group. For example, in one preferred embodiment where the olefin corresponds to Formula 2-EWG(a), $R_3$ and $R_4$ may be any of the moieties identified as preferred or alternative embodiments for $R_3$ and $R_4$ in connection with Formula 1. In one particularly preferred embodiment where the olefin corresponds to Formula 2-EWG(a), $R_3$ and $R_4$ are both hydrogen.

In an embodiment where the olefin corresponds to Formula 2, a substituent on the β-carbon may be an electron withdrawing group. In an example of this embodiment, $R_4$ is an electron withdrawing group, and the olefin corresponds to Formula 2-EWG(b):

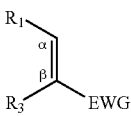

Formula 2-EWG(b)

wherein $R_1$ is a substituent of the α-carbon of the ethylenic bond; $R_3$ and EWG are substituents of the β-carbon of the ethylenic bond; $R_1$ and $R_3$ are independently hydrogen, hydrocarbyl, substituted hydrocarbyl, heterocyclo, or an electron withdrawing group; and EWG is an electron withdrawing group. For example, in one preferred embodiment where the olefin corresponds to Formula 2-EWG(b), $R_1$ and $R_3$ may be any of the moieties identified as preferred or alternative embodiments for $R_1$ and $R_3$ in connection with Formula 1. In one particularly preferred embodiment where the olefin is as depicted in Formula 2-EWG(b), $R_1$ and $R_3$ are both hydrogen.

In a preferred embodiment where the olefin corresponds to Formula 1, one but only one of the substituents on the α-carbon of the ethylenic bond is hydrogen, and one but only one of the substituents on the β-carbon of the ethylenic bond is hydrogen. In an example of this embodiment, $R_2$ is hydrogen, one of $R_3$ and $R_4$ is hydrogen, and the olefin corresponds to Formula 3-trans or Formula 3-cis, respectively:

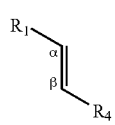

Formula 3-trans

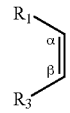

Formula 3-cis wherein $R_1$ is a substituent of the α-carbon of the ethylenic bond; $R_3$ and $R_4$ are substituents of the β-carbon of the ethylenic bond; and $R_1$, $R_3$ and $R_4$ are independently hydrogen, hydrocarbyl, substituted hydrocarbyl, heterocyclo, or an electron withdrawing group.

For example, in one preferred embodiment where the olefin corresponds to Formula 3-trans, $R_1$ and $R_4$ may be any of the moieties identified as preferred or alternative embodiments for $R_1$ and $R_4$ in connection with Formula 1. In another preferred embodiment where the olefin corresponds to Formula 3-trans, at least one of $R_1$ and $R_4$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^aR^b$ where $R^a$ and $R^b$ are independently hydrogen, hydrocarbyl, substituted hydrocarbyl or heterocyclo. In a further preferred embodiment where the olefin corresponds to Formula 3-trans, at least one of $R_1$ and $R_4$ is —C(O)CH$_3$, —C(O)OCH$_3$, —C(O)OC$_2$H$_5$, or —C(O)N$R^aR^b$, where $R^a$ and $R^b$ are independently alkyl. In an even more preferred embodiment where the olefin corresponds to Formula 3-trans, at least one of $R_1$ and $R_4$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl.

In an alternative example of a preferred embodiment where the olefin corresponds to Formula 3-cis, $R_1$ and $R_3$ may be any of the moieties identified as preferred or alternative embodiments for $R_1$ and $R_3$ in connection with Formula 1. In another preferred embodiment where the olefin corresponds to Formula 3-cis, at least one of $R_1$ and $R_3$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^aR^b$ where $R^a$ and $R^b$ are independently hydrogen, hydrocarbyl, substituted hydrocarbyl or heterocyclo. In a further preferred embodiment where the olefin corresponds to Formula 3-cis, at least one of $R_1$ and $R_3$ is —C(O)CH$_3$, —C(O)OCH$_3$, —C(O)OC$_2$H$_5$, or —C(O)N$R^aR^b$, where $R^a$ and $R^b$ are independently alkyl. In an even more preferred embodiment where the olefin corresponds to Formula 3-cis, at least one of $R_1$ and $R_3$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl.

In an embodiment where the olefin corresponds to Formula 3-trans or Formula 3-cis, $R_1$, $R_3$, or $R_4$ may be an electron withdrawing group. In an example of this embodiment where, for example, $R_1$ is an electron withdrawing group, the olefin corresponds to Formula 3-trans-EWG or Formula 3-cis-EWG:

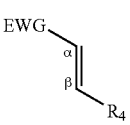

Formula 3-trans-EWG

Formula 3-cis-EWG

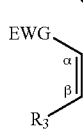

wherein EWG is a substituent of the α-carbon of the ethylenic bond; $R_3$ and $R_4$ are substituents of the β-carbon of the ethylenic bond; $R_3$ and $R_4$ are independently hydrogen, hydrocarbyl, substituted hydrocarbyl, heterocyclo, or an electron withdrawing group; and EWG is an electron withdrawing group.

For example, in one preferred embodiment where the olefin corresponds to Formula 3-trans-EWG, $R_4$ may be any of the moieties identified as preferred or alternative embodiments for $R_4$ in connection with Formula 1. In a particularly preferred embodiment where the olefin corresponds to Formula 3-trans-EWG, $R_4$ is hydrogen.

In another example, in one preferred embodiment where the olefin corresponds to Formula 3-cis-EWG, $R_3$ may be any of the moieties identified as preferred or alternative embodiments for $R_3$ in connection with Formula 1. In a particularly preferred embodiment where the olefin corresponds to Formula 3-cis-EWG, $R_3$ is hydrogen.

In an embodiment where the olefin corresponds to Formula 1 and the olefin is a terminal olefin, either both of $R_1$ and $R_2$, or both of $R_3$ and $R_4$, are hydrogen. In an example of this embodiment, $R_1$ and $R_2$ are both hydrogen, and the olefin corresponds to Formula 4:

Formula 4

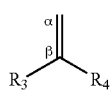

wherein $R_3$ and $R_4$ are substituents of the β-carbon of the ethylenic bond; and $R_3$ and $R_4$ are independently hydrogen, hydrocarbyl, substituted hydrocarbyl, heterocyclo, or an electron withdrawing group. For example, in one preferred embodiment where the olefin corresponds to Formula 4, $R_3$ and $R_4$ may be any of the moieties identified as preferred or alternative embodiments for $R_3$ and $R_4$ in connection with Formula 1.

In one preferred embodiment where the olefin corresponds to Formula 4, at least one of $R_3$ and $R_4$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^aR^b$ where $R^a$ and $R^b$ are independently hydrogen, hydrocarbyl, substituted hydrocarbyl or heterocyclo. In a further preferred embodiment where the olefin corresponds to Formula 4, at least one of $R_3$ and $R_4$ is —C(O)CH$_3$, —C(O)OCH$_3$, —C(O)OC$_2$H$_5$, or —C(O)N$R^aR^b$, where $R^a$ and $R^b$ are independently alkyl. In an even more preferred embodiment corresponding Formula 4, at least one of $R_3$ and $R_4$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl.

In one embodiment, the olefin corresponds to Formula 4, and one of $R_3$ and $R_4$ is an electron withdrawing group. In an example of this embodiment, $R_4$ is an electron withdrawing group and the olefin corresponds to Formula 4-EWG:

Formula 4-EWG

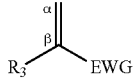

wherein $R_3$ and EWG are substituents of the β-carbon of the ethylenic bond; $R_3$ is hydrogen, hydrocarbyl, substituted hydrocarbyl, heterocyclo, or an electron withdrawing group; and EWG is an electron withdrawing group. For example, in one preferred embodiment where the olefin corresponds to Formula 4-EWG, $R_3$ may be any of the moieties identified as preferred or alternative embodiments for $R_3$ in connection with Formula 1. Where the olefin corresponds to Formula 4-EWG, $R_3$ is, in a particularly preferred embodiment, hydrogen.

In another preferred embodiment, the olefin corresponds to Formula 1, three of $R_1$, $R_2$, $R_3$, and $R_4$ are hydrogen, and the olefin is a terminal olefin. In an example of this embodiment, $R_1$, $R_2$, and $R_4$ are hydrogen and the olefin corresponds to Formula 5:

Formula 5

wherein $R_3$ is a substituent of the β-carbon of the ethylenic bond; and $R_3$ is hydrogen, hydrocarbyl, substituted hydrocarbyl, heterocyclo, or an electron withdrawing group. For example, in one preferred embodiment where the olefin corresponds to Formula 5, $R_3$ may be any of the moieties identified as preferred or alternative embodiments for $R_3$ in connection with Formula 1.

In another preferred embodiment where the olefin corresponds to Formula 5, $R_3$ is alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —N$R^aR^b$ where $R^a$ and $R^b$ are independently hydrogen, hydrocarbyl, substituted hydrocarbyl or heterocyclo. In a further preferred embodiment in which the olefin corresponds to Formula 5, $R_3$ is —C(O)CH$_3$, —C(O)OCH$_3$, —C(O)OC$_2$H$_5$, or —C(O)N$R^aR^b$, where $R^a$ and $R^b$ are independently alkyl. In an even more preferred embodiment where the olefin corresponds to Formula 5, $R_3$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl.

In an embodiment where the olefin corresponds to Formula 5, and $R_3$ is an electron withdrawing group, the olefin corresponds to Formula 5-EWG:

Formula 5-EWG

wherein EWG is a substituent of the β-carbon of the ethylenic bond; and EWG is an electron withdrawing group.

In general, the olefin's electron withdrawing group(s), EWG, as depicted in Formulae 1-EWG, 2-EWG(a), 2-EWG (b), 3-trans-EWG, 3-cis-EWG, 4-EWG, and 5-EWG, and described in connection with Formulae 1, 2, 3-trans, 3-cis, 4 and 5, is any substituent that draws electrons away from the ethylenic bond. Exemplary electron withdrawing groups include hydroxy, alkoxy, mercapto, halogens, carbonyls, sulfonyls, nitrile, quaternary amines, nitro, trihalomethyl, imine, amidine, oxime, thioketone, thioester, or thioamide. In one embodiment, the electron withdrawing group(s) is/are hydroxy, alkoxy, mercapto, halogen, carbonyl, sulfonyl, nitrile, quaternary amine, nitro, or trihalomethyl. In another embodiment, the electron withdrawing group(s) is/are halogen, carbonyl, nitrile, quaternary amine, nitro, or trihalomethyl. In another embodiment, the electron withdrawing group(s) is/are halogen, carbonyl, nitrile, nitro, or trihalomethyl. When the electron withdrawing group is alkoxy, it generally corresponds to the formula —OR where R is an alkyl group. When the electron withdrawing group is mercapto, it generally corresponds to the formula —SR where R is hydrogen, hydrocarbyl, substituted hydrocarbyl or heterocyclo. When the electron withdrawing group is a halogen atom, the electron withdrawing group may be fluoro, chloro, bromo, or iodo; typically, it will be fluoro or chloro. When the electron withdrawing group is a carbonyl, it may be an aldehyde (C(O)H), ketone (C(O)R), ester (C(O)OR), acid (C(O)OH), acid halide (C(O)X), amide (C(O)NR$^a$R$^b$), or anhydride (C(O)OC(O)R) where R is hydrocarbyl, substituted hydrocarbyl or heterocyclo, R$^a$ and R$^b$ are independently hydrogen, hydrocarbyl, substituted hydrocarbyl or heterocyclo, and X is a halogen atom. When the electron withdrawing group is a sulfonyl, it may be an acid (SO$_3$H) or a derivative thereof (SO$_2$R) where R is hydrocarbyl, substituted hydrocarbyl or heterocyclo. When the electron withdrawing group is a quaternary amine, it generally corresponds to the formula —N$^+$R$^a$R$^b$R$^c$ where R$^a$, R$^b$ and R$^c$ are independently hydrogen, hydrocarbyl, substituted hydrocarbyl or heterocyclo. When the electron withdrawing group is a trihalomethyl, it is preferably trifluoromethyl or trichloromethyl. In each of the foregoing exemplary electron withdrawing groups containing the variable "X", in one embodiment, X may be chloro or fluoro, preferably fluoro. In each of the foregoing exemplary electron withdrawing groups containing the variable "R", R may be alkyl. In each of the foregoing exemplary electron withdrawing groups containing the variable "R$^a$", "R$^b$", or "R$^c$", R$^a$, R$^b$, and R$^c$ may independently be hydrogen or alkyl.

In accordance with one preferred embodiment, the electron withdrawing group(s) is/are a halide, aldehyde, ketone, ester, carboxylic acid, amide, acyl chloride, trifluoromethyl, nitrile, sulfonic acid, ammonia, amine, or a nitro group. In this embodiment, the electron withdrawing group(s) correspond to one of the following chemical structures: X, C(O)H, C(O)R, C(O)OR, C(O)OH, C(O)X, C(X)$_3$, —CN, SO$_3$H, N$^+$H$_3$, N$^+$(R)$_3$, or N$^+$O$_2$ where R is hydrocarbyl, substituted hydrocarbyl or heterocyclo and X is halogen.

As illustrated more fully in the examples, the diastereo- and enantio-selectivity can be influenced, at least in part, by selection of the metal porphyrin complex. Similarly, stereoselectivity of the reaction may also be influenced by the selection of chiral porphyrin ligands with desired electronic, steric, and chiral environments. Accordingly, the catalytic system of the present invention may advantageously be used to control stereoselectivity.

In one embodiment, the metal of the metal porphyrin complex is a transition metal. Thus, for example, the metal may be any of the 30 metals in the 3d, 4d, and 5d transition metal series of the Periodic Table of the Elements, including the 3d series that includes Sc, Ti, V, Cr, Mn, Fe, Co, Ni, Cu, and Zn; the 4d series that includes Y, Zr, Nb, Mo, Tc, Ru, Rh, Pd, Ag and Cd; and the 5d series that includes Lu, Hf, Ta, W, Re, Os, Ir, Pt, Au and Hg. In some embodiments, M is a transition metal from the 3d series. In some preferred embodiments, M is selected from the group consisting of Co, Zn, Fe, Ru, Mn, and Ni. In even more preferred embodiments, M is selected from the group consisting of Co, Fe, and Ru. In further preferred embodiments, M is Co.

The porphyrin with which the transition metal is complexed may be any of a wide range of porphyrins known in the art. Exemplary porphyrins are described in U.S. Patent Publication Nos. 2005/0124596 and 2006/0030718 and U.S. Pat. No. 6,951,935 (each of which is incorporated herein by reference, in its entirety).

In a preferred embodiment, the porphyrin is complexed with cobalt. The porphyrin with which cobalt is complexed may be any of a wide range of porphyrins known in the art. Exemplary porphyrins are described in U.S. Patent Publication Nos. 2005/0124596 and 2006/0030718 and U.S. Pat. No. 6,951,935 (each of which is incorporated herein by reference, in its entirety). Exemplary porphyrins are also described in Chen et al., Bromoporphyrins as Versatile Synthons for Modular Construction of Chiral Porphyrins: Cobalt-Catalyzed Highly Enantioselective and Diastereoselective Cyclopropanation (J. Am. Chem. Soc. 2004), which is incorporated herein by reference in its entirety.

In one embodiment, the metal porphyrin complex is a cobalt(II) porphyrin complex. In one particularly preferred embodiment, the cobalt porphyrin complex is a chiral porphyrin complex corresponding to the following structure:

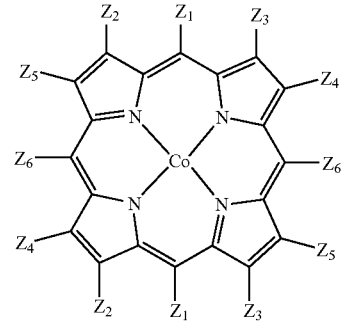

wherein each $Z_1$, $Z_2$, $Z_3$, $Z_4$, $Z_5$ and $Z_6$ are each independently selected from the group consisting of X, H, alkyl, substituted alkyls, arylalkyls, aryls and substituted aryls; and X is selected from the group consisting of halogen, trifluoromethanesulfonate (OTf), haloaryl and haloalkyl. In a preferred embodiment, $Z_2$, $Z_3$, $Z_4$ and $Z_5$ are hydrogen, $Z_1$ is a substituted phenyl, $Z_6$ is substituted phenyl, and $Z_1$ and $Z_6$ are different. In one particularly preferred embodiment, $Z_2$, $Z_3$, $Z_4$ and $Z_5$ are hydrogen, $Z_1$ is substituted phenyl, $Z_6$ is substituted phenyl, $Z_1$ and $Z_6$ are different, and the porphyrin is a chiral porphyrin. In one even further preferred embodiment, $Z_2$, $Z_3$, $Z_4$ and $Z_5$ are hydrogen, $Z_1$ is substituted phenyl, $Z_6$ is substituted phenyl, $Z_1$ and $Z_6$ are different and the porphyrin has D$_2$-symmetry.

In a preferred embodiment, $Z_1$ is selected from the group consisting of

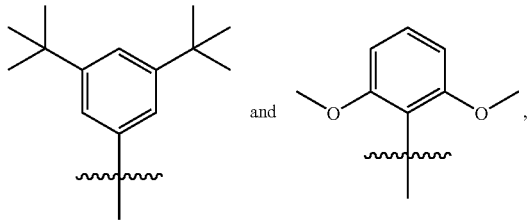

wherein

denotes the point of attachment to the porphyrin complex.

In a preferred embodiment, $Z_6$ is selected from the group consisting of
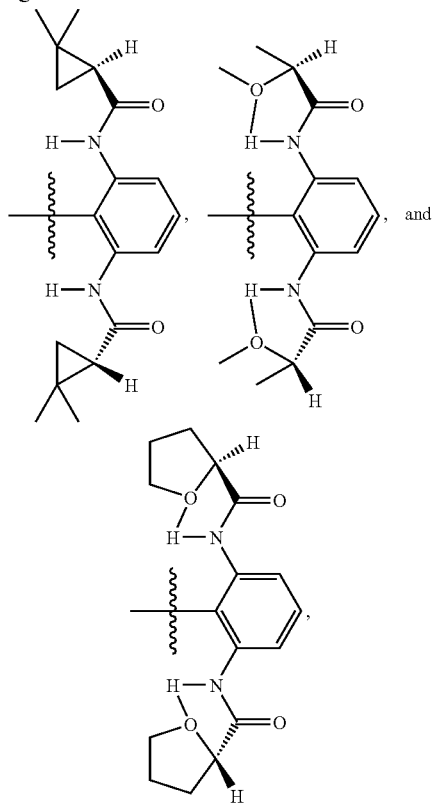
wherein
denotes the point of attachment to the porphyrin complex.
Exemplary cobalt (II) porphyrins include the following, designated [Co(P1)], [Co(P2)], [Co(P3)], [Co(P4)], [Co(P5)], and [Co(P6)], shown in Formulae A, B, C, D, E, and F, respectively:
Formula A
[Co(P1)]
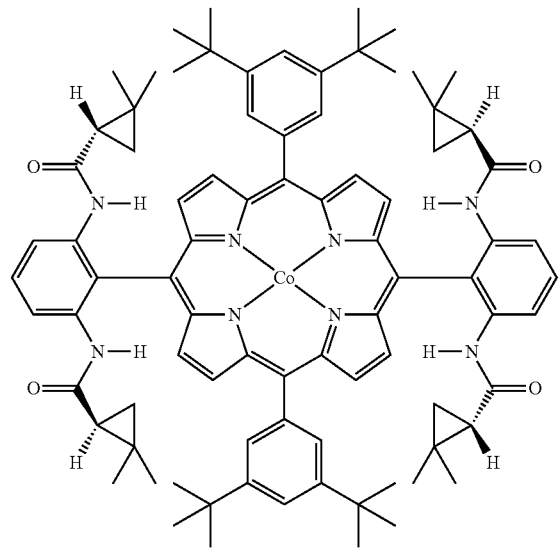
Formula B
[Co(P2)]
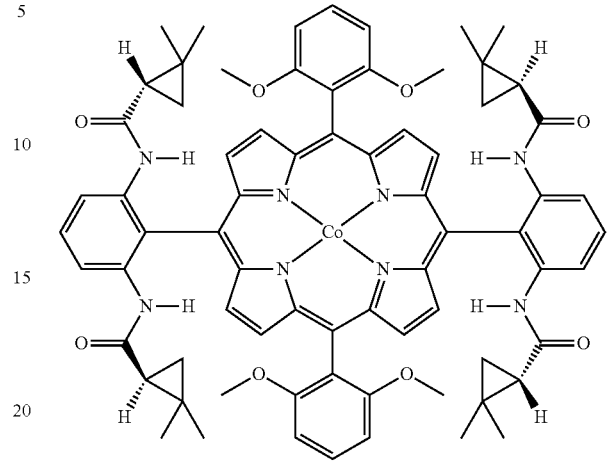
Formula C
[Co(P3)]
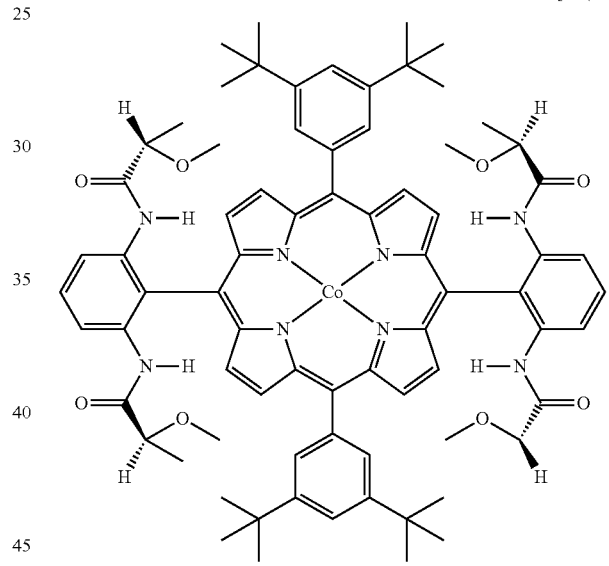
Formula D
[Co(P4)]
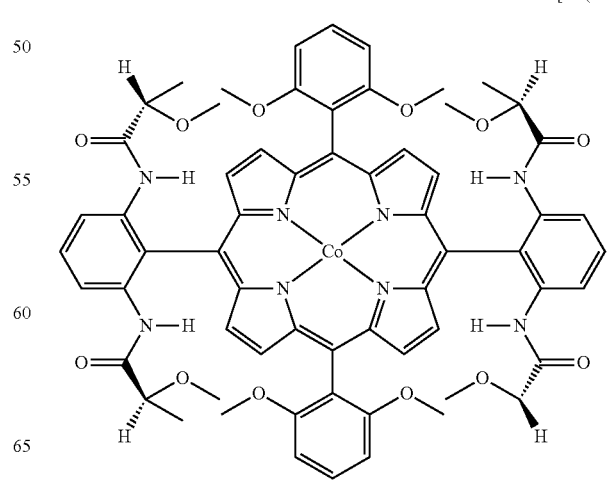

Formula E

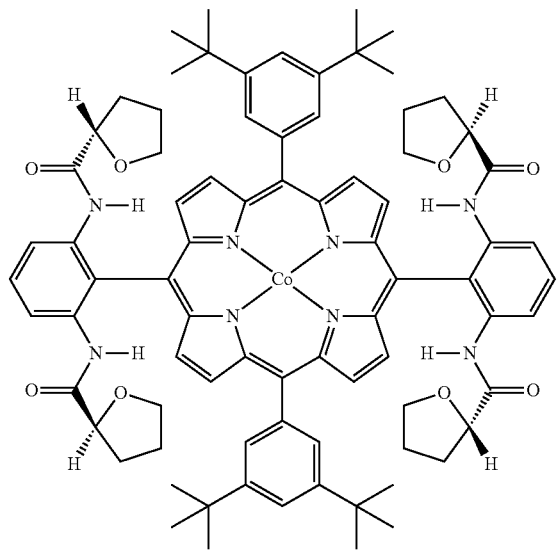

[Co(P5)]

Formula F

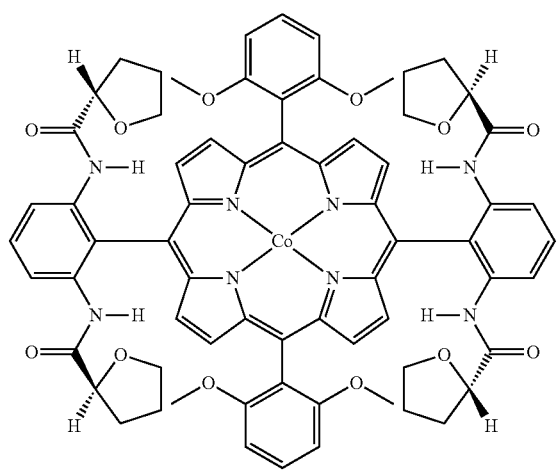

[Co(P6)]

In general, the olefin is cyclopropanated with a carbene source, where the carbene source is an electron acceptor substituted nitro diazo reagent. Preferably, the olefin is cyclopropanated with an α-nitro carbene source, wherein the α denotes that the nitro group is on the α-carbon of the carbene source. More preferably, the carbene source, or precursor, is an α-nitro diazo reagent (also sometimes referred to herein as a diazo compound) wherein the carbene is generated from the carbene precursor by the removal of $N_2$ as nitrogen gas from the solution. Generally, the carbene precursor, an electron acceptor substituted nitro diazo reagent, corresponds to the following Formula 7:

Formula 7

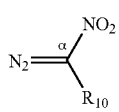

wherein the nitro group (—$NO_2$), the diazo group (—$N_2$), and $R_{10}$ are all substituents of the α-carbon; and $R_{10}$ is an electron acceptor.

In one embodiment, $R_{10}$ is any electron acceptor known in the art. In another embodiment, $R_{10}$ is an aldehyde, ketone, ester, or carboxylic acid.

Preferably, the carbene precursor is an α-nitro diazo carbonyl reagent. When the carbene precursor is an α-nitro diazo carbonyl reagent, it corresponds to the following Formula 8:

Formula 8

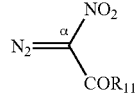

wherein the nitro group (—$NO_2$), the diazo group (—$N_2$), and —$COR_{11}$ are all substituents of the α-carbon; $R_{11}$ is hydrogen, hydrocarbyl, substituted hydrocarbyl, heterocyclo, halogen, —$OR_{20}$, —$NR^aR^b$, or —$OC(O)R_{21}$; $R_{20}$ is hydrogen, hydrocarbyl, substituted hydrocarbyl, or heterocyclo; $R^a$ and $R^b$ are independently hydrogen, hydrocarbyl, substituted hydrocarbyl or heterocyclo; and $R_{21}$ is hydrocarbyl, substituted hydrocarbyl or heterocyclo.

In one embodiment, $R_{11}$ is hydrogen. In a preferred embodiment, $R_{11}$ is alkyl or substituted alkyl, more typically lower alkyl. In another preferred embodiment, $R_{11}$ is aryl or alkaryl, more typically lower aryl. In yet another preferred embodiment, $R_{11}$ is alkoxy or hydroxy.

In a preferred embodiment, the carbene precursor corresponds to Formula 7 and $R_{10}$ is an ester; stated differently, the carbene precursor corresponds to Formula 8 and $R_{11}$ is an alkoxy group. In this embodiment, the carbene precursor corresponds to Formula 9:

Formula 9

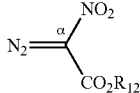

wherein the nitro group (—$NO_2$), the diazo group (—$N_2$), and —$CO_2R_{12}$ are all substituents of the α-carbon; and $R_{12}$ is hydrogen, hydrocarbyl, substituted hydrocarbyl, or heterocyclo.

In one embodiment, $R_{12}$ is hydrogen. In another embodiment, $R_{12}$ is alkyl or substituted alkyl, more typically lower alkyl. In another embodiment, $R_{12}$ is aryl or alkaryl, more typically lower aryl. In a preferred embodiment, $R_{12}$ is ethyl, methyl, butyl, or propyl, typically tert-butyl and iso-propyl.

In some embodiments, the carbene precursor is selected from the group consisting of the α-nitro analogs of diazo ethylacetate, diazo-t-butylacetate, 2,6-di-tert-butyl-4-methylphenyl diazoacetate, methyl phenyldiazoacetate, ethyl diazoacetate, diethyl diazomalonate, and trimethylsilyldiazomethane. In some embodiments, the diazo compound is selected from one of the α-nitro analogs of diazo ethylacetate and diazo t-butylacetate. Other exemplary diazo acetates include the α-nitro analogs of 2,3,4-trimethyl-3-pentyl diazoacetate, methyl diazoacetate, 2,5-dimethyl-4-buten-1-yl diazoacetate, 3-(diazoacetyl)amino propionate, and (diazoacetyl)amino acetate.

In accordance with one embodiment of the present invention, an olefin is converted to a cyclopropane as illustrated in Reaction Scheme A:

Reaction Scheme A

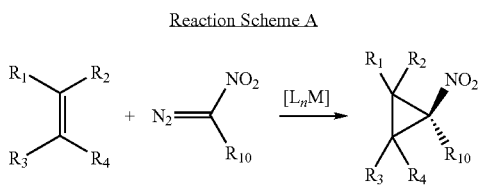

wherein [$L_nM$] is a metal porphyrin complex; $R_1$, $R_2$, $R_3$, and $R_4$ are as previously defined in connection with Formula 1; and $R_{10}$ is as previously defined in connection with Formula 7.

In one embodiment, where the reaction proceeds as illustrated in Reaction Scheme A, [$L_nM$] is a metal porphyrin complex wherein the metal is a transition metal, preferably Co, Fe, or Ru. In a preferred embodiment where the reaction proceeds as illustrated in Reaction Scheme A, [$L_nM$] is a cobalt(II) porphyrin complex. In another embodiment where the reaction proceeds as illustrated in Reaction Scheme A, the porphyrin complex of [$L_nM$] is a chiral porphyrin complex. In a further embodiment where the reaction proceeds as illustrated in Reaction Scheme A, the porphyrin complex of [$L_nM$] has $D_2$-symmetry. In a preferred embodiment where the reaction proceeds as illustrated in Reaction Scheme A, [$L_nM$] is a chiral cobalt(II) porphyrin complex with $D_2$-symmetry. In a further preferred embodiment where the reaction proceeds as illustrated in Reaction Scheme A, [$L_nM$] corresponds to one of the porphyrin complexes in Formulae A-F.

In accordance with a preferred embodiment of the present invention, an olefin is converted to a cyclopropane as illustrated in Reaction Scheme B:

Reaction Scheme B

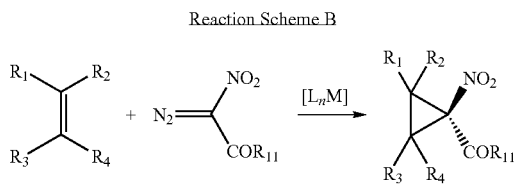

wherein [$L_nM$] is as previously described in connection with Reaction Scheme A; $R_1$, $R_2$, $R_3$, and $R_4$ are as previously defined in connection with Reaction Scheme A; and $R_{11}$ is as previously defined in connection with Formula 8.

In another preferred embodiment of the present invention, an olefin is converted to a cyclopropane as illustrated in Reaction Scheme C:

Reaction Scheme C

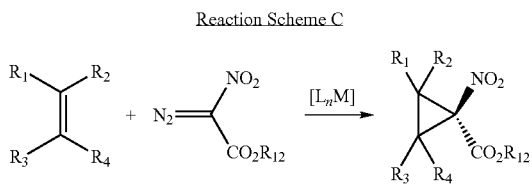

wherein [$L_nM$] is a as previously described in connection with Reaction Scheme A; $R_1$, $R_2$, $R_3$, and $R_4$ are as previously described in connection with Reaction Scheme A; and $R_{12}$ is as previously defined in connection with Formula 9.

In preferred embodiments wherein an olefin is converted to a cyclopropane as depicted in Reaction Scheme A, B, or C, [$L_nM$] is a metal porphyrin complex wherein the metal is a transition metal, typically cobalt; the olefin is styrene, substituted styrene, an α,β-unsaturated ester, or an α,β-unsaturated ketone; and the α-carbon of the nitro diazo reagent is substituted with an aldehyde, ketone, ester, or carboxylic acid. In an even more preferred embodiment where the reaction is as illustrated in Reaction Scheme A, B, or C, [$L_nM$] is a cobalt porphyrin complex; at least one of $R_1$, $R_2$, $R_3$, and $R_4$ is an electron withdrawing group, alkyl, aryl, substituted phenyl, —C(O)$R_{22}$, or —C(O)O$R_{22}$ wherein $R_{22}$ is hydrogen, optionally substituted alkyl, optionally substituted alkenyl, optionally substituted alkynyl, optionally substituted aryl, or —NR$^a$R$^b$ wherein R$^a$ and R$^b$ are independently hydrogen, hydrocarbyl, substituted hydrocarbyl or heterocyclo; and the nitro diazo reagent corresponds to Formula 8 wherein $R_{11}$ is hydrogen, hydrocarbyl, substituted hydrocarbyl, heterocyclo, halogen, —O$R_{20}$, —NR$^a$R$^b$, or —OC(O)$R_{21}$ where $R_{20}$ is hydrogen, hydrocarbyl, substituted hydrocarbyl, or heterocyclo, R$^a$ and R$^b$ are independently hydrogen, hydrocarbyl, substituted hydrocarbyl or heterocyclo, and $R_{21}$ is hydrocarbyl, substituted hydrocarbyl or heterocyclo. In another preferred embodiment where the reaction proceeds as shown in Reaction Scheme A, B, or C, [$L_nM$] is a cobalt porphyrin complex corresponding to one of the cobalt porphyrin complexes depicted in Formulae A-F; at least one of $R_1$, $R_2$, $R_3$, and $R_4$ is phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, or dimethylcarbamoyl; and the nitro diazo reagent corresponds to Formula 9 wherein $R_{12}$ is alkyl or substituted alkyl, preferably ethyl, methyl, butyl, or propyl.

In another embodiment, an olefin is converted to a cyclopropane as illustrated in Reaction Scheme D:

Reaction Scheme D

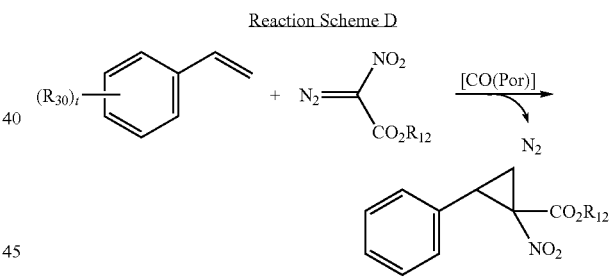

wherein $R_{12}$ is as previously defined in connection with Formula 9; $R_{30}$ is hydrogen, hydrocarbyl, substituted hydrocarbyl, halo, or heterocyclo; t is any integer from 0 to 5, inclusive; and [Co(Por)] is a cobalt porphyrin complex. In preferred embodiments where the reaction proceeds as illustrated in Reaction Scheme D, [Co(Por)] is one of Formula A-F.

In one embodiment, $R_{30}$ is alkyl or substituted alkyl. In a preferred embodiment, $R_{30}$ is methyl, butyl, t-butyl, or trifluoromethyl. In an alternately embodiment, $R_{30}$ is halo, typically chloro, bromo, or fluoro. In another preferred embodiment, $R_{30}$ is nitro.

As stated above, t can be any integer from 0 to 5; more typically, t is 1 to 5. For example, in an embodiment, t is 1 and $R_{30}$ is methyl or butyl. In another example, t is 1 and $R_{30}$ is halo, such as bromo, chloro, or fluoro. In yet another example, t is 5 and $R_{30}$ is halo, preferably fluoro.

In another embodiment, an olefin is converted to a cyclopropane as illustrated in Reaction Scheme E:

Reaction Scheme E

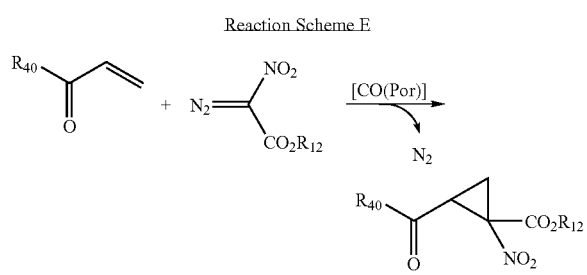

wherein $R_{12}$ is as previously defined in connection with Formula 9; $R_{40}$ is hydrogen, hydrocarbyl, substituted hydrocarbyl, halo, or heterocyclo; and [Co(Por)] is a cobalt porphyrin complex. In preferred embodiments where the reaction proceeds as illustrated in Reaction Scheme D, [Co(Por)] is one of Formula A-F.

In one embodiment, $R_{40}$ is alkyl or substituted alkyl. In another embodiment, $R_{40}$ is —$NR^aR^b$ where $R^a$ and $R^b$ are independently hydrogen, hydrocarbyl, substituted hydrocarbyl or heterocyclo. In a preferred embodiment, $R_{40}$ is aryl, typically phenyl or substituted phenyl. In another preferred embodiment, $R_{40}$ is ethyl, phenyl, methoxy, ethoxy, or —$N(CH_3)_2$.

The reaction products resulting from cyclopropanation of an olefin with an α-nitro-diazoacetate are valuable precursors for a number of useful compounds, including the synthetically and biologically important cyclopropane α-amino acids. Alpha-amino acids have an amino group and a carboxylate group attached to the same carbon, known as the α-carbon. These α-amino acids are biologically important, as the twenty most common amino acids found in proteins are all α-amino acids. The reaction proceeds from the cyclopropane as illustrated in Reaction Scheme F:

Reaction Scheme F

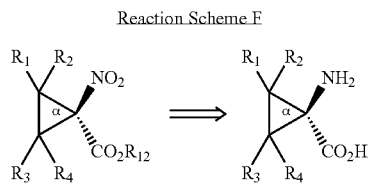

wherein $R_1$, $R_2$, $R_3$ and $R_4$ are as previously defined in connection with Formula 1; and $R_{12}$ is as previously defined in connection with Formula 9.

The reaction products resulting from cyclopropanation of an olefin with an α-nitro diazoacetate are also valuable precursors for the synthetically and biologically important aminocyclopropanes. Aminocyclopropanes have an amino group on the carbon known as the α-carbon. Aminocyclopropanes can be formed from the cyclopropanation product through the reduction of the nitro (—$NO_2$) group on the α-carbon, and elimination of the ester group on the α-carbon. The reaction proceeds from the cyclopropane to the aminocyclopropane as illustrated in Reaction Scheme G:

Reaction Scheme G

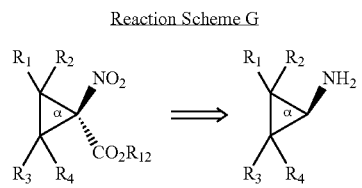

wherein $R_1$, $R_2$, $R_3$ and $R_4$ are as previously described in connection with Formula 1; and $R_{12}$ is as previously described in connection with Formula 9.

Thus, the cyclopropanes resulting from the metal porphyrin-catalyzed reaction of an olefin with an α-nitro-diazo reagent are demonstrated precursors for the synthetically and biologically important cyclopropane α-amino acids and aminocyclopropanes. This process is illustrated generally in Reaction Scheme H:

Reaction Scheme H

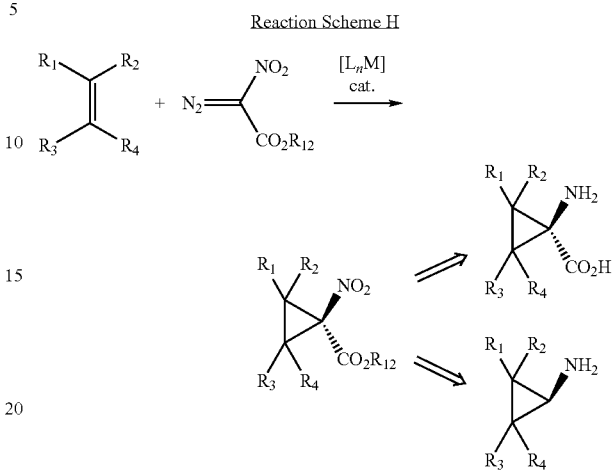

wherein $[L_nM]$ is as previously defined in connection with Reaction Scheme A; $R_1$, $R_2$, $R_3$, and $R_4$ are as previously defined in connection with Formula 1; and $R_{12}$ is as previously defined in connection with Formula 9.

In a preferred embodiment, the olefin is a terminal olefin. In an example of this embodiment, the olefin corresponds to Formula 1 and $R_3$ and $R_4$ are hydrogen, and the process illustrated generally in Reaction Scheme H is illustrated generally by Reaction Scheme J:

Reaction Scheme J

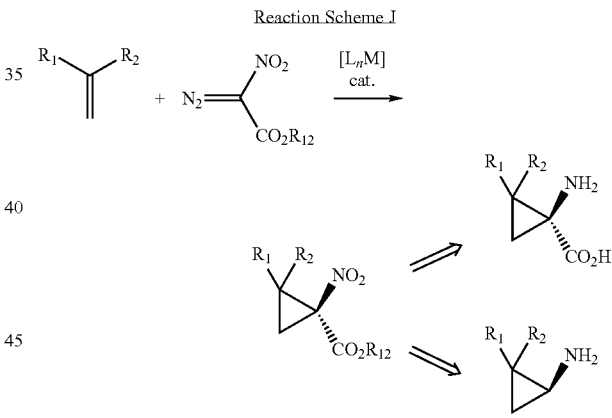

wherein $[L_nM]$, $R_1$, $R_2$, and $R_{12}$ are as previously defined in connection with Reaction Scheme H.

Aliphatic nitro compounds can be reduced to aliphatic amines using any of several different reagents which are well known to those of skill in the art. In a preferred embodiment, the nitro group is catalytically reduced using, for example, a source of hydrogen and a catalyst such as palladium on carbon, zinc (0), Raney nickel, or iron. The reaction conditions appropriate for the reduction of a nitro moiety to an amine moiety will depend on the substrate. In one embodiment, the reduction of a nitro moiety to an amine moiety takes place in mild reducing conditions. A variety of acids, such as acetic acid, hydrochloric acid, or ammonium chloride, and solvents, such as methanol or 2-propanol, can be used, and the combination selected will depend on the substrate.

Esters can be hydrolyzed to yield carboxylic acids, either by aqueous base or by aqueous acid. Ester hydrolysis in basic solution is referred to as saponification, and occurs through the nucleophilic acyl substitution pathway, while acid-catalyzed ester hydrolysis can occur via several different pathways. Appropriate conditions for ester hydrolysis are well known to those of skill in the art. Similarly, the appropriate conditions for reducing carbonyl compounds are well known to those of skill in the art.

In the interests of brevity, each of the foregoing Formulae were presented without full stereochemistry. Since the compounds of the present invention have several asymmetric carbons, it is known to those skilled in the art that the compounds of the present invention having asymmetric carbon atoms may exist in diastereomeric, racemic, or optically active forms. All of these forms are contemplated within the scope of this invention. More specifically, the present invention includes the enantiomers, diastereomers, racemic mixtures, and other optically active mixtures of the compounds disclosed herein.

In summary, we have developed a general and highly asymmetric Z cyclopropanation process with α-nitrodiazoacetates catalyzed by [Co(P1)]. This represents the first highly effective and selective catalytic system for asymmetric cyclopropanation with acceptor/acceptor-substituted diazo reagents as the carbene source. In addition to the well-documented synthetic utility of the resulting cyclopropane α-nitro esters, the demonstration of α-nitrodiazoacetates as effective and selective carbene sources for cyclopropanation may stimulate further studies that will lead to the general use of acceptor/acceptor-substituted diazo reagents for catalytic carbene transfers.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Initial efforts were focused on the systematic evaluation of various catalytic conditions for the cyclopropanation of styrene with ethyl α-nitrodiazoacetates (ENDAs) by different [Co(Por)] (Tables 1 and S1). While the ineffectiveness of Co(tpp) for the reaction might be expected (Table 1, entry 1), it was a disappointing revelation that [Co(P6)], which was previously shown to be the best catalyst for asymmetric cyclopropanation with diazosulfones, gave an even poorer result (Table 1, entry 7). However, in contrast to previous systems, it was noted that the Z cyclopropane was the major product. Subsequent experiments with other $D_2$-symmetric chiral porphyrins with varied environments revealed a dramatic ligand effect (Table 1, entries 2-7). Among them (as shown in Formulae A-F), [Co(P1)] proved to be the optimal catalyst, producing the Z dominant cyclopropane α-nitroester (Z/E=91:09) in 99% yield and 81% ee (Table 1, entry 2). The [Co(P1)]-based catalytic system was further improved by optimizing other reaction conditions (Table 1, entries 8-12 and Table S1).

The effectiveness of [Co(Por)] could perhaps be rationalized as a consequence of two potential N—H...O hydrogen-bonding interactions between two of the chiral amide N—H moieties on the P1 ligand with both the N=O (—$NO_2$ group) and the C=O (—$CO_2Et$ group) units of the carbene moiety, respectively. These interactions occur in a postulated metallocarbene intermediate and would promote the carbene formation from the less reactive diazo reagent and rigidify the intermediate towards its subsequent reaction with the olefin substrate, which would lead to a more effective and selective catalytic process. (A similar mechanism has been proposed for a nitrene transfer reaction. See Ruppel et al., Org. Lett. 2008, 10, 1995.) While similar interactions would also exist in the [Co(P2)]-catalyzed reaction, the intercomponent hydrogen bonds between amides and carbene moieties in the cases of [Co(P3)]-[Co(P6)] would be inhibited or largely reduced as a result of the competitive N—H...O hydrogen-bonding interactions within the chiral amide units of the ligands (Formulae A-F).

Based on the optimized reaction conditions (Table 1), the substrate scope of the [Co(P1)]-based catalytic system was then examined. It was shown that the catalytic process could be successfully applied to different alkene substrates with various NDA derivatives (Table 2 and Table S2). For example, in addition to styrene, various styrene derivatives containing groups at different ring positions could be effectively cyclopropanated with EDNA or tert-butyl α-nitrodiazoacetates (t-BDNAs) (Table 2, entries 1-17). As one of unique catalytic properties associated with [Co(Por)]-based system, even the extremely electron-deficient pentafluorostyrene could be used as a substrate, albeit resulting in a somewhat relatively lower yield (Table 2, entry 18). The use of α-methylstyrene allowed the stereoselective construction of a cyclopropane structure containing two contiguous quaternary stereogenic centers (Table 2, entry 19). When the cyclopropanation reaction was conducted under solvent-free conditions, aliphatic alkenes, which are typically challenging substrates for this reaction, were also successfully converted into the desired cyclopropanes with good diastereo- and enantioselectivity although in moderate yields (Table 2, entries 20-21). When 1,2-dichloroethane was used as solvent, electron-deficient olefins such as α,β-unsaturated esters and amides, which represent another series of challenging substrates, could be cyclopropanated as well, but with diminished diastereoselectivity (Table 2, entries 22-24). In most cases, however, the corresponding cyclopropane α-nitroesters were obtained predominantly as Z isomers in high yields with high enantioselectivities (Tables 2 and S2).

TABLE 1

Asymmetric Z-cyclopropanation of styrene with ethyl α-nitrodiazoacetate by $D_2$-symmetric chiral cobalt(II) porphyrins.[a]

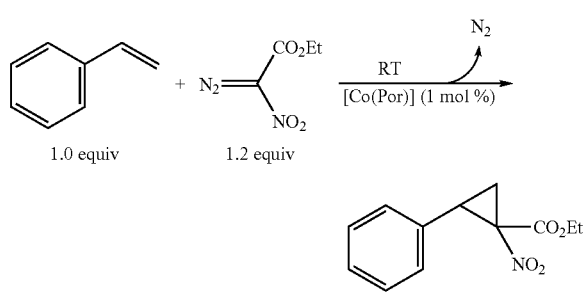

| Entry | [Co(Por)][b] | Solvent | Yield [%][c] | Z/E[d] | ee [%][e] |
|---|---|---|---|---|---|
| 1 | [Co(tpp)] | $CH_2Cl_2$ | 15 | 58:42 | — |
| 2 | [Co(P1)] | $CH_2Cl_2$ | 99 | 91:09 | 81 |
| 3 | [Co(P2)] | $CH_2Cl_2$ | 99 | 91:09 | 58 |
| 4 | [Co(P3)] | $CH_2Cl_2$ | 20 | 67:33 | 33 |
| 5 | [Co(P4)] | $CH_2Cl_2$ | 69 | 81:19 | 47 |
| 6 | [Co(P5)] | $CH_2Cl_2$ | 31 | 66:34 | −23 |

TABLE 1-continued

Asymmetric Z-cyclopropanation of styrene with ethyl α-nitrodiazoacetate by D$_2$-symmetric chiral cobalt(II) porphyrins.[a]

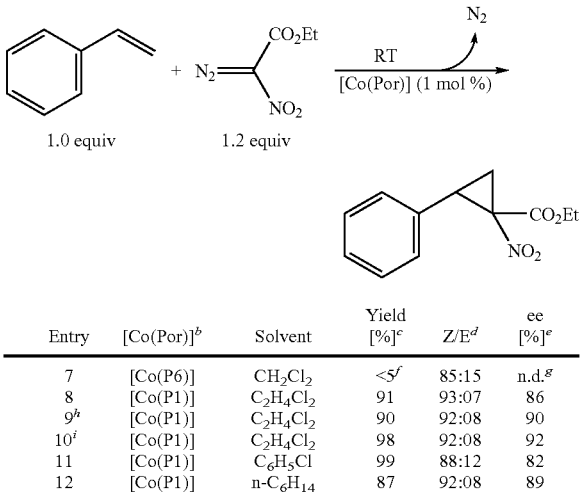

| Entry | [Co(Por)][b] | Solvent | Yield [%][c] | Z/E[d] | ee [%][e] |
|---|---|---|---|---|---|
| 7 | [Co(P6)] | CH$_2$Cl$_2$ | <5[f] | 85:15 | n.d.[g] |
| 8 | [Co(P1)] | C$_2$H$_4$Cl$_2$ | 91 | 93:07 | 86 |
| 9[h] | [Co(P1)] | C$_2$H$_4$Cl$_2$ | 90 | 92:08 | 90 |
| 10[i] | [Co(P1)] | C$_2$H$_4$Cl$_2$ | 98 | 92:08 | 92 |
| 11 | [Co(P1)] | C$_6$H$_5$Cl | 99 | 88:12 | 82 |
| 12 | [Co(P1)] | n-C$_6$H$_14$ | 87 | 92:08 | 89 |

[a]Performed at RT for 24 h using 1 mol % [Co(Por)] under N$_2$ with 1.0 equiv of styrene (0.25 M) and 1.2 equiv of ENDA.
[b]See Formulae A-F for structures.
[c]Isolated yields.
[d]Determined by NMR.
[e]ee of Z isomer determined by HPLC using a chiral stationary phase.
[f]Estimated by NMR.
[g]Not determined.
[h]0° C.; 2 mol % [Co(Por)].
[i]−20° C.; 5 mol % [Co(Por)].

TABLE S1

Asymmetric (Z)-Cyclopropanation of Styrene with Ethyl α-Nitro-Diazoacetate by D$_2$-Symmetric Chiral Cobalt(II) Porphyrins.[a]

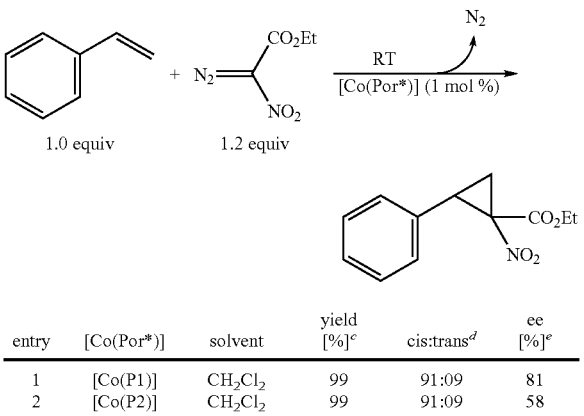

| entry | [Co(Por*)] | solvent | yield [%][c] | cis:trans[d] | ee [%][e] |
|---|---|---|---|---|---|
| 1 | [Co(P1)] | CH$_2$Cl$_2$ | 99 | 91:09 | 81 |
| 2 | [Co(P2)] | CH$_2$Cl$_2$ | 99 | 91:09 | 58 |

TABLE S1-continued

Asymmetric (Z)-Cyclopropanation of Styrene with Ethyl α-Nitro-Diazoacetate by D$_2$-Symmetric Chiral Cobalt(II) Porphyrins.[a]

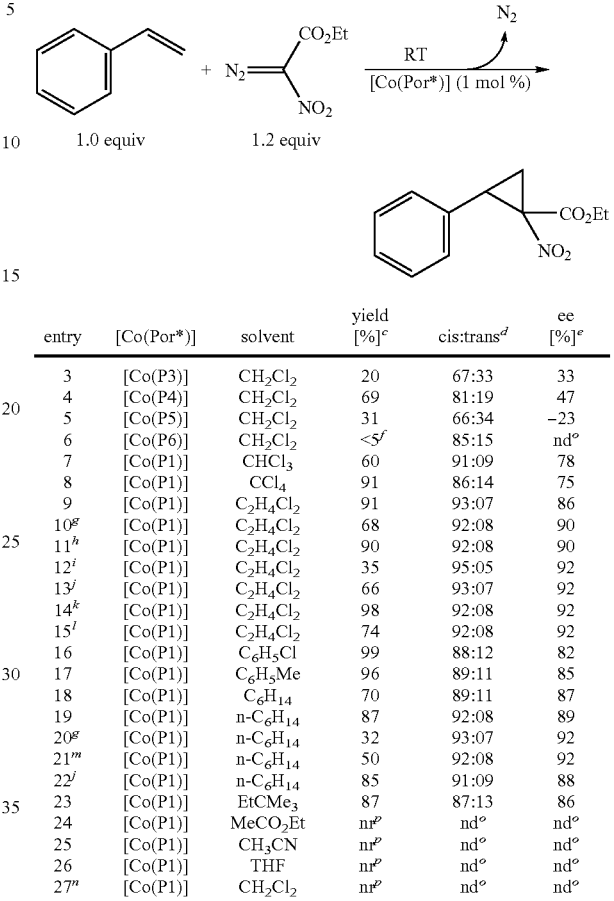

| entry | [Co(Por*)] | solvent | yield [%][c] | cis:trans[d] | ee [%][e] |
|---|---|---|---|---|---|
| 3 | [Co(P3)] | CH$_2$Cl$_2$ | 20 | 67:33 | 33 |
| 4 | [Co(P4)] | CH$_2$Cl$_2$ | 69 | 81:19 | 47 |
| 5 | [Co(P5)] | CH$_2$Cl$_2$ | 31 | 66:34 | −23 |
| 6 | [Co(P6)] | CH$_2$Cl$_2$ | <5[f] | 85:15 | nd[o] |
| 7 | [Co(P1)] | CHCl$_3$ | 60 | 91:09 | 78 |
| 8 | [Co(P1)] | CCl$_4$ | 91 | 86:14 | 75 |
| 9 | [Co(P1)] | C$_2$H$_4$Cl$_2$ | 91 | 93:07 | 86 |
| 10[g] | [Co(P1)] | C$_2$H$_4$Cl$_2$ | 68 | 92:08 | 90 |
| 11[h] | [Co(P1)] | C$_2$H$_4$Cl$_2$ | 90 | 92:08 | 90 |
| 12[i] | [Co(P1)] | C$_2$H$_4$Cl$_2$ | 35 | 95:05 | 92 |
| 13[j] | [Co(P1)] | C$_2$H$_4$Cl$_2$ | 66 | 93:07 | 92 |
| 14[k] | [Co(P1)] | C$_2$H$_4$Cl$_2$ | 98 | 92:08 | 92 |
| 15[l] | [Co(P1)] | C$_2$H$_4$Cl$_2$ | 74 | 92:08 | 92 |
| 16 | [Co(P1)] | C$_6$H$_5$Cl | 99 | 88:12 | 82 |
| 17 | [Co(P1)] | C$_6$H$_5$Me | 96 | 89:11 | 85 |
| 18 | [Co(P1)] | C$_6$H$_14$ | 70 | 89:11 | 87 |
| 19 | [Co(P1)] | n-C$_6$H$_14$ | 87 | 92:08 | 89 |
| 20[g] | [Co(P1)] | n-C$_6$H$_14$ | 32 | 93:07 | 92 |
| 21[m] | [Co(P1)] | n-C$_6$H$_14$ | 50 | 92:08 | 92 |
| 22[j] | [Co(P1)] | n-C$_6$H$_14$ | 85 | 91:09 | 88 |
| 23 | [Co(P1)] | EtCMe$_3$ | 87 | 87:13 | 86 |
| 24 | [Co(P1)] | MeCO$_2$Et | nr[p] | nd[o] | nd[o] |
| 25 | [Co(P1)] | CH$_3$CN | nr[p] | nd[o] | nd[o] |
| 26 | [Co(P1)] | THF | nr[p] | nd[o] | nd[o] |
| 27[n] | [Co(P1)] | CH$_2$Cl$_2$ | nr[p] | nd[o] | nd[o] |

[a]Performed at RT for 24 h using 1 mol % [Co(Por*)] under N$_2$ with 1.0 equiv of styrene and 1.2 equiv of ENDA. [styrene] = 0.25 M.
[b]See Formulae A-F for structures.
[c]Isolated yields.
[d]Determined by NMR.
[e](Z) isomer ee was determined by chiral HPLC.
[f]Estimated by NMR.
[g]0° C.
[h]0° C.; 2 mol %.
[i]−20° C.
[j]−20° C.; 2 mol %.
[k]−20° C.; 5 mol %.
[l]−20° C.; 5.0 equiv styrene.
[m]0° C. to RT.
[n]0.5 equiv DMAP.
[o]No determination.
[p]No reaction.

TABLE 2

[Co(P1)]-Catalyzed Diastereo- and Enantioselective Cyclopropanation of Different Alkenes with α-Nitro-Diazoacetates.[a]

| Entry | Cyclopropane | R | Yield [%][b] | Z/E[i] | ee [%][d] | [α][e] |
|---|---|---|---|---|---|---|
| 1 | | Et | 87 | 92:08 | 89 | (−) |
| 2[g,h] | | Et | 93 | 92:08 | 92 | (−) |
| 3 | | tBu | 91 | >99:1 | 91 | (−) |
| 4[g,h] | | tBu | 97 | >99:1 | 94 | (−) |

TABLE 2-continued

[Co(P1)]-Catalyzed Diastereo- and Enantioselective Cyclopropanation of Different Alkenes with α-Nitro-Diazoacetates.[a]

| Entry | Cyclopropane | R | Yield [%][b] | Z/E[i] | ee [%][d] | [α][e] |
|---|---|---|---|---|---|---|
| 5[g,h] | (4-Me-C6H4 cyclopropane with CO2R and NO2) | Et | 86[k] | 93:07 | 90 | (−) |
| 6[h] | | tBu | 90 | >99:1 | 92 | (−) |
| 7[g,h] | (3-Me-C6H4 cyclopropane with CO2R and NO2) | Et | 91 | 96:04 | 91 | (−) |
| 8[g,h] | (2-Me-C6H4 cyclopropane with CO2R and NO2) | Et | 82 | 92:08 | 91 | (−) |
| 9[g,h] | (4-tBu-C6H4 cyclopropane with CO2R and NO2) | Et | 83 | 92:08 | 90 | (−) |
| 10[h] | | tBu | 87 | >99:1 | 92 | (−) |
| 11[g,h] | (4-Br-C6H4 cyclopropane with CO2R and NO2) | Et | 84 | 91:09 | 90 | (−) |
| 12[g,h] | (4-Cl-C6H4 cyclopropane with CO2R and NO2) | Et | 82 | 91:09 | 90 | (−) |
| 13[g,h] | (4-F-C6H4 cyclopropane with CO2R and NO2) | Et | 87 | 91:09 | 90 | (−) |
| 14[g,h] | (4-F3C-C6H4 cyclopropane with CO2R and NO2) | Et | 88 | 92:08 | 90 | (−) |
| 15[h] | | tBu | 98 | 96:04 | 88 | (−) |
| 16 | (3-O2N-C6H4 cyclopropane with CO2R and NO2) | Et | 90 | 91:09 | 94 | (−)[f] |
| 17[g,h] | | Et | 81 | 93:07 | 95 | (−)[f] |
| 18[h,i] | (pentafluorophenyl cyclopropane with CO2R and NO2) | Et | 51 | 90:10 | 82 | (−) |

TABLE 2-continued

[Co(P1)]-Catalyzed Diastereo- and Enantioselective Cyclopropanation of Different Alkenes with α-Nitro-Diazoacetates.[a]

| Entry | Cyclopropane | R | Yield [%][b] | Z/E[i] | ee [%][d] | [a][e] |
|---|---|---|---|---|---|---|
| 19 | Me, Ph, CO$_2$R, NO$_2$ | Et | 70[k] | 94:06 | 83 | (−) |
| 20[h,m] | Et, CO$_2$R, NO$_2$ | tBu | 45 | 92:08 | ≥80[n] | (−) |
| 21[h,m] | Ph, CO$_2$R, NO$_2$ | tBu | 43 | 92:08 | ≥86[n] | (+) |
| 22[h,j] | Me-O-C(O)-, CO$_2$R, NO$_2$ | Et | 42 | 53:47 | 88 | (−) |
| 23[h,j] | Et-O-C(O)-, CO$_2$R, NO$_2$ | Et | 62 | 56:44 | 88 | (−) |
| 24[h,j] | Me$_2$N-C(O)-, CO$_2$R, NO$_2$ | Et | 92 | 63:37 | 75 | (−) |

[a] Performed in n-hexane at RT for 24 h under N$_2$ using [Co(P1)] 1 mol % with 1.0 equiv of alkene 0.25 M and 1.2 equiv of NDA.
[b] Isolated yields.
[c] Determined by NMR.
[d] ee of Z isomer determined by HPLC using a chiral stationary phase.
[e] Sign of optical rotation.
[f] [1S,2S] absolute configuration determined by X-ray crystal structural analysis and optical rotation.
[g] 0° C. → RT.
[h] 5 mol %.
[j] In C$_2$H$_4$Cl$_2$.
[k] Determined by NMR.
[l] Alkene/NDA = 5:1; 48 h.
[m] No solvent; 48 h.
[n] ee of Z isomer determined by chiral HPLC via derivatization.

TABLE S2

[Co(P1)]-Catalyzed Diastereo- and Enantioselective Cyclopropanation of Different Alkenes with α-Nitro-Diazoacetates.[a]

| entry | cyclopropane | R | yield [%][b] | cis:trans[c] | ee [%][d] | [a][e] |
|---|---|---|---|---|---|---|
| 1 | Ph-cyclopropane-CO$_2$R, NO$_2$ | Me | <5 | 89:11 | 78 | (−) |
| 2[j] | | Me | 71 | 89:11 | 75 | (−) |
| 3 | | Et | 87 | 92:08 | 89 | (−) |
| 4[g,h] | | Et | 93 | 92:08 | 92 | (−) |
| 5 | | i-Pr | 36 | 92:08 | 90 | (−) |
| 6 | | t-Bu | 91 | >99:1 | 91 | (−) |
| 7[g,i] | | t-Bu | 58 | >99:1 | 94 | (−) |
| 8[g,h] | | t-Bu | 97 | >99:1 | 94 | (−) |

TABLE S2-continued

[Co(P1)]-Catalyzed Diastereo- and Enantioselective Cyclopropanation of Different Alkenes with α-Nitro-Diazoacetates.[a]

| entry | cyclopropane | R | yield [%][b] | cis:trans[c] | ee [%][d] | [a][e] |
|---|---|---|---|---|---|---|
| 9 | 4-Me-C6H4 cyclopropane CO2R/NO2 | Et | 70 | 90:10 | 88 | (−) |
| 10[g,h] | | Et | 86 | 93:07 | 90 | (−) |
| 11[h] | | t-Bu | 90 | >99:1 | 92 | (−) |
| 12 | 3-Me-C6H4 cyclopropane CO2R/NO2 | Et | 49 | 91:09 | 88 | (−) |
| 13[i] | | Et | 95 | 93:07 | 87 | (−) |
| 14[g,h] | | Et | 91 | 96:04 | 91 | (−) |
| 15 | 2-Me-C6H4 cyclopropane CO2R/NO2 | Et | 47 | 90:10 | 89 | (−) |
| 16[i] | | Et | 81 | 87:13 | 88 | (−) |
| 17[g,h] | | Et | 82 | 92:08 | 91 | (−) |
| 18 | 4-tBu-C6H4 cyclopropane CO2R/NO2 | Et | 79 | 92:08 | 88 | (−) |
| 19[j] | | Et | 99 | 93:07 | 85 | (−) |
| 20[g,h] | | Et | 83 | 92:08 | 90 | (−) |
| 21[h] | | t-Bu | 87 | >99:1 | 92 | (−) |
| 22 | 4-Br-C6H4 cyclopropane CO2R/NO2 | Et | 75 | 91:09 | 87 | (−) |
| 23[g,h] | | Et | 84 | 91:09 | 90 | (−) |
| 24[h] | | t-Bu | 91 | 98:02 | 82 | (−) |
| 25 | 4-Cl-C6H4 cyclopropane CO2R/NO2 | Et | 81 | 89:11 | 88 | (−) |
| 26[g,h] | | Et | 82 | 91:09 | 90 | (−) |
| 27 | 4-F-C6H4 cyclopropane CO2R/NO2 | Et | 55 | 92:08 | 88 | (−) |
| 28[i] | | Et | 82 | 90:10 | 86 | (−) |
| 29[g,h] | | Et | 87 | 91:09 | 90 | (−) |
| 30 | 4-F3C-C6H4 cyclopropane CO2R/NO2 | Et | 84 | 90:10 | 89 | (−) |
| 31[g,h] | | Et | 88 | 92:08 | 90 | (−) |
| 32[h] | | t-Bu | 98 | 96:04 | 88 | (−) |
| 33 | 3-O2N-C6H4 cyclopropane CO2R/NO2 | Et | 90 | 91:09 | 94 | (−)[f] |
| 34[g,h] | | Et | 81 | 93:07 | 95 | (−)[f] |
| 35[h] | | t-Bu | 95 | 98:02 | 78 | (−) |
| 36 | C6F5 cyclopropane CO2R/NO2 | Et | 16[k] | >99:1 | 83 | (−) |
| 37[h,l] | | Et | 51 | 90:10 | 82 | (−) |

TABLE S2-continued

[Co(P1)]-Catalyzed Diastereo- and Enantioselective Cyclopropanation of Different Alkenes with α-Nitro-Diazoacetates.[a]

| entry | cyclopropane | R | yield [%][b] | cis:trans[c] | ee [%][d] | [a][e] |
|---|---|---|---|---|---|---|
| 38 | Me, Ph, CO$_2$R, NO$_2$ | Et | 70[k] | 94:06 | 83 | (−) |
| 39[h,m] | Et, CO$_2$R, NO$_2$ | Et | 56 | 60:40 | 70[n] | (−) |
| 40[h,m] | | t-Bu | 45 | 92:08 | 80[n] | (−) |
| 41[h,m] | Ph, CO$_2$R, NO$_2$ | Et | 47 | 60:40 | 69 | (+) |
| 42[h,m] | | t-Bu | 43 | 92:08 | 86[n] | (+) |
| 43[h,o] | Me-O-C(O)-, CO$_2$R, NO$_2$ | Et | 41 | 33:67 | 80 | (−) |
| 44[h,p] | | Et | 49 | 53:47 | 85 | (−) |
| 45[h,j] | | Et | 42 | 53:47 | 88 | (−) |
| 46[h,j] | Et-O-C(O)-, CO$_2$R, NO$_2$ | Et | 62 | 56:44 | 88 | (−) |
| 47[h,j] | Me$_2$N-C(O)-, CO$_2$R, NO$_2$ | Et | 92 | 63:37 | 75 | (−) |

[a] Performed in n-hexane at RT for 24 h using 1 mol % [Co(P1)] under N$_2$ with 1.0 equiv of alkene and 1.2 equiv of NDA. [alkene] = 0.25 M.
[b] Isolated yields.
[c] Cis:Trans ratio determined by NMR.
[d] (Z) isomer ee determined by chiral HPLC.
[e] Sign of optical rotation.
[f] [1S,2S] absolute configuration by X-ray crystal structural analysis and optical rotation.
[g] 0° C. to RT.
[h] 5 mol %.
[i] 2 mol %.
[j] In C$_2$H$_4$Cl$_2$.
[k] NMR yield.
[l] Alkene:NDA = 5:1; 48 h.
[m] Neat; 48 h.
[n] (Z) isomer ee determined by chiral HPLC via derivatization.
[o] In C$_6$H$_5$Cl.
[p] In CH$_2$Cl$_2$.

General Considerations. All reactions were carried out under a nitrogen atmosphere in oven-dried glassware following standard Schlenk techniques. Hexane (Reagent Plus, ≥99%) was used directly from Sigma-Aldrich Chemical Co. Chlorobenzene was distilled under nitrogen from calcium hydride. α-Nitro-diazoacetates were synthesized following the reported procedure. (Charette et al., Helv. Chim. Acta 2002, 85, 4468.) Thin layer chromatography was performed on Merck TLC plates (silica gel 60 F254). Flash column chromatography was performed with ICN silica gel (60 Å, 230-400 mesh, 32-63 μm). Proton and carbon nuclear magnetic resonance spectra ($^1$H NMR and $^{13}$NMR) were recorded on a Bruker 250-MHz instrument and referenced with respect to internal TMS standard. HPLC measurements were carried out on a Shimadzu HPLC system with Whelk-O1, Chiralcel OD-H, OJ-H, and AD-H columns. Infrared spectra were measured with a Nicolet Avatar 320 spectrometer with a Smart Miracle accessory. HRMS data was obtained on an Agilent 1100 LC/MS ESI/TOF mass spectrometer with electrospray ionization.

General Procedures for Cyclopropanation of Styrene. Catalyst (1 mol %) was placed in an oven-dried, resealable Schlenk tube. The tube was capped with a Teflon screwcap, evacuated, and backfilled with nitrogen. The screwcap was replaced with a rubber septum, and 1.0 equivalent of styrene (0.25 mmol) in 1.0 mL Hexane was added via syringe, followed by 1.2 equivalents of diazo compound (0.30 mmol). The tube was purged with nitrogen for 1 min and its contents were stirred at room temperature. After the reaction finished, the resulting mixture was concentrated and the residue was purified by flash silica gel chromatography to give the product.

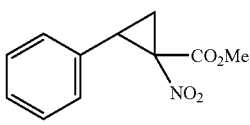

Methyl 1-nitro-2-phenylcyclopropanecarboxylate: [Z]-: $[\alpha]^{20}_D=-52.6$ (c=0.52, CHCl$_3$). $^1$H NMR (250 MHz, CDCl$_3$): δ 7.26-7.13 (m, 5H), 3.83 (s, 3H), 3.42 (t, J=9.5 Hz, 1H), 2.61 (dd, J$_1$=7.0 Hz, J$_2$=9.3 Hz, 1H), 1.97 (dd, J$_1$=7.0 Hz, J$_2$=10.0 Hz, 1H). $^{13}$C NMR (62.5 MHz, CDCl$_3$): δ 165.9, 131.3, 128.7, 128.7, 128.3, 53.8, 33.9, 20.1. IR (neat, cm$^{-1}$): 1741, 1544, 1438, 1293, 1152. HRMS (ESI) ([M+H]$^+$) Calcd. for C$_{11}$H$_{12}$NO$_4$: 222.0766, Found 222.0761. HPLC analysis: ee=75%. OD-H (95% hexanes: 5% isopropanol, 1.0 mL/min) [Z]-isomer: t$_{major}$=8.7 min, t$_{minor}$=10.7 min.

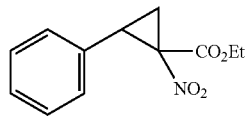

Ethyl 1-nitro-2-phenylcyclopropanecarboxylate: [Z]-: $[\alpha]^{20}_D=-56.4$ (c=0.67, CHCl$_3$). $^1$H NMR (250 MHz, CDCl$_3$): δ 7.26-7.15 (m, 5H), 4.33 (m, 2H), 3.40 (t, J=9.8 Hz, 1H), 2.60 (dd, J$_1$=6.8 Hz, J$_2$=9.0 Hz, 1H), 1.94 (dd, J$_1$=7.0 Hz, J$_2$=10.0 Hz, 1H), 1.27 (t, J=7.3 Hz, 3H). $^{13}$C NMR (62.5 MHz, CDCl$_3$): δ 165.4, 131.5, 128.7, 128.6, 128.4, 72.7, 63.3, 33.7, 20.0, 14.0. IR (neat, cm$^{-1}$): 1743, 1542, 1295, 1151. HRMS (ESI) ([M+H]$^+$) Calcd. for C$_{12}$H$_{14}$NO$_4$: 236.0923, Found 236.0921. HPLC analysis: ee=88%. OD-H (95% hexanes: 5% isopropanol, 1.0 mL/min) [Z]-isomer: t$_{major}$=6.8 min, t$_{minor}$=8.3 min.

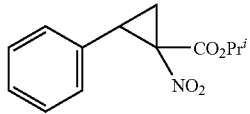

iso-Propyl 1-nitro-2-phenylcyclopropanecarboxylate: [Z]-: $[\alpha]^{20}_D=-53.8$ (c=0.34, CHCl$_3$). $^1$H NMR (250 MHz, CDCl$_3$): δ7.25-7.13 (m, 5H), 5.12 (m, 1H), 3.39 (t, J=9.5 Hz, 1H), 2.59 (dd, J$_1$=7.0 Hz, J$_2$=9.3 Hz, 1H), 1.92 (dd, J$_1$=7.0 Hz, J$_2$=10.0 Hz, 1H), 1.27-1.24 (m, 6H). $^{13}$C NMR (62.5 MHz, CDCl$_3$): δ 164.8, 131.5, 128.7, 128.6, 128.3, 71.5, 33.4, 21.7, 21.5, 19.9. IR (neat, cm$^{-1}$): 1718, 1540, 1285, 1152. HRMS (ESI) ([M+H]$^+$) Calcd. for C$_{13}$H$_{16}$NO$_4$: 250.1079, Found 250.1069. HPLC analysis: ee=90%. OD-H (95% hexanes: 5% isopropanol, 1.0 mL/min) [Z]-isomer: t$_{major}$=5.6 min, t$_{minor}$=6.7 min.

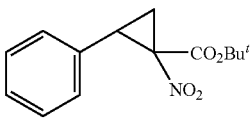

t-Butyl 1-nitro-2-phenylcyclopropanecarboxylate: [Z]-: $[\alpha]^{20}_D=-47.4$ (c=0.16, CHCl$_3$). $^1$H NMR (250 MHz, CDCl$_3$): δ 7.25-7.13 (m, 5H), 3.33 (t, J=9.5 Hz, 1H), 2.53 (dd, J$_1$=7.0 Hz, J$_2$=9.0 Hz, 1H), 1.87 (dd, J$_1$=7.0 Hz, J$_2$=9.5 Hz, 1H), 1.46 (s, 9H). $^{13}$C NMR (62.5 MHz, CDCl$_3$): δ 164.1, 131.8, 128.7, 128.5, 128.3, 84.8, 33.0, 27.9, 19.7. IR (neat, cm$^{-1}$): 1726, 1538, 1260, 1145. HRMS (ESI) ([M+NH$_4$]$^+$) Calcd. for C$_{14}$H$_{21}$N$_2$O$_4$: 281.1501, Found 281.1494. HPLC analysis: ee=91%. OD-H (95% hexanes: 5% isopropanol, 1.0 mL/min) [Z]-isomer: t$_{major}$=4.8 min, t$_{minor}$=5.8 min.

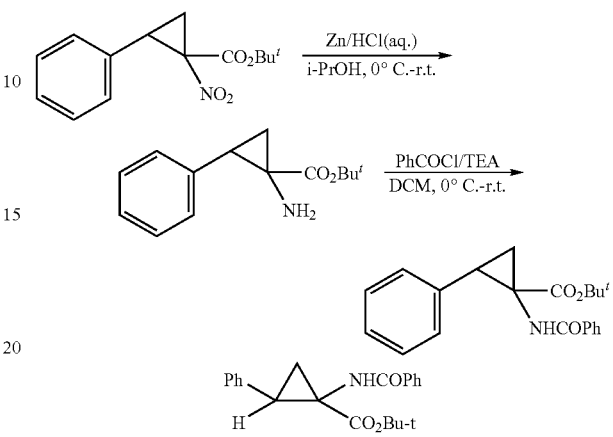

(Z)-t-butyl 1-benzamido-2-phenylcyclopropanecarboxylate: (The reduction step followed the literature; Wurz R. P., Charette A. B., J. Org. Chem. 2004, 69, 1262-1269.) Cooled by ice water, [Z]-tert-Butyl 1-nitro-2-phenylcyclopropanecarboxylate (29 mg, 0.11 mmol, 91% ee) was dissolved in 2.2 mL of i-PrOH and treated with 1 N HCl (1.1 mL, 10 equiv). Zinc dust (145 mg, 2.2 mmol, 20 equiv) was added in one portion and the solution allowed stirring for 2 h at room temperature. The suspension was quenched by addition of a saturated solution of NaHCO$_3$ (5 mL). The aqueous phase was extracted with dichloromethane (5 mL 3), the combined organic extracts were dried over anhydrous MgSO$_4$ and filtered, and concentrate the solvent to about 2.0 ml under reduced pressure. Then cooled by ice-water, to the about DCM solution, 45 µL Et$_3$N was added, followed by 30 µL PhCOCl, and the solution allowed to stir for 1 h at room temperature. The resulting solution was quenched by addition of water (2 drops), remove the solvent and water at 40° C. under reduced pressure. The crude residue was then chromatographed on silica gel pretreated with 1:3 EtOAc/hexanes, affording the corresponding product (36 mg, 97%). [Z]-: $[\alpha]^{20}_D=-25.2$ (c=0.385, CHCl$_3$). $^1$H NMR (250 MHz, CDCl$_3$): δ 7.41-7.18 (m, 10H), 5.86 (s, br, 1H), 2.88 (t, J=8.5 Hz, 1H), 2.20 (dd, J$_1$=6.0 Hz, J$_2$=9.5 Hz, 1H), 1.75 (dd, J$_1$=6.0 Hz, J$_2$=7.5 Hz, 1H), 1.40 (s, 9H). $^{13}$C NMR (62.5 MHz, CDCl$_3$): δ 170.6, 168.4, 134.7, 134.4, 131.6, 128.7, 128.6, 128.5, 127.5, 126.8, 81.9, 39.8, 32.2, 28.1, 20.9. HRMS (ESI) ([M+H]$^+$) Calcd. for O$_{21}$H$_{24}$NO$_3$: 338.1756, Found 338.1754. HPLC analysis: ee=83%. AD-H (95% hexanes: 5% isopropanol, 1.0 mL/min) [Z]-isomer: t$_{major}$=19.0 min, t$_{minor}$=27.0 min.

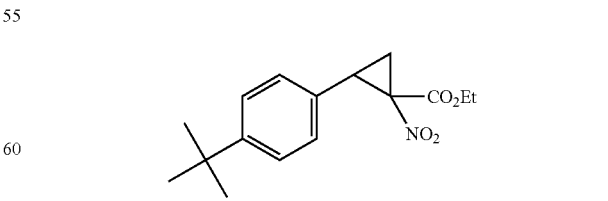

Ethyl 2-(4-t-butylphenyl)-1-nitrocyclopropanecarboxylate: [Z]-: $[\alpha]^{20}_D=-53.3$. (c=0.86, CHCl$_3$). $^1$H NMR (250 MHz, CDCl$_3$): δ 7.25 (d, J=8.5 Hz, 2H), 7.07 (d, J=8.5 Hz, 2H), 4.33-4.23 (m, 2H), 3.37 (t, J=9.5 Hz, 1H), 2.58 (dd, $J_1$=7.0 Hz, $J_2$=9.3 Hz, 1H), 1.93 (dd, $J_1$=7.0 Hz, $J_2$=9.8 Hz, 1H), 1.27 (t, J=7.3 Hz, 3H), 1.20 (s, 9H). $^{13}$C NMR (62.5 MHz, CDCl$_3$): δ 165.5, 151.6, 128.3, 128.0, 125.7, 72.7, 63.2, 34.6, 33.6, 31.3, 20.1, 14.0. IR (neat, cm$^{-1}$): 1740, 1548, 1378, 1294, 1155. HRMS (ESI) ([M+H]$^+$) Calcd. for C$_{16}$H$_{22}$NO$_4$: 292.1549, Found 292.1552. HPLC analysis: ee=88%. OD-H (98.5% hexanes: 1.5% isopropanol, 1.0 mL/min) [Z]-isomer: $t_{major}$=6.7 min, $t_{minor}$=7.5 min.

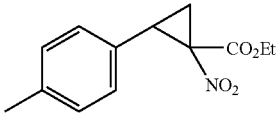

Ethyl 1-nitro-2-p-tolylcyclopropanecarboxylate: [α]$^{20}_D$=−43.9. (c=1.24, CHCl$_3$). $^1$H NMR (250 MHz, CDCl$_3$): δ7.20-7.03 (m, 4H), 4.28-4.25 (m, 2H), 3.37 (t, J=9.5 Hz, 1H), 2.57 (dd, $J_1$=7.0 Hz, $J_2$=10.5 Hz, 1H), 2.23 (s, 3H), 1.92 (dd, $J_1$=7.0 Hz, $J_2$=10.0 Hz, 1H), 1.26 (t, J=7.3 Hz, 3H). $^{13}$C NMR (62.5 MHz, CDCl$_3$): δ 165.4, 138.5, 129.4, 128.4, 128.2, 72.7, 63.2, 33.6, 21.2, 20.0, 14.0. IR (neat, cm$^{-1}$): 1736, 1543, 1290, 1151. HRMS (ESI) ([M+H]$^+$) Calcd. for C$_{13}$H$_{16}$NO$_4$: 250.1079, Found 250.1093. HPLC analysis: ee=88%. OD-H (95% hexanes: 5% isopropanol, 1.0 mL/min) [Z]-isomer: $t_{major}$=5.7 min, $t_{minor}$=6.5 min.

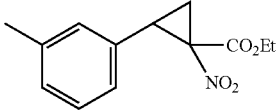

Ethyl 1-nitro-2-m-tolylcyclopropanecarboxylate: [Z]-: [α]$^{20}_D$=−51.8. (c=0.97, CHCl$_3$). $^1$H NMR (250 MHz, CDCl$_3$): δ7.18-6.91 (m, 4H), 4.32-4.23 (m, 2H), 3.36 (t, J=9.5 Hz, 1H), 2.58 (dd, $J_1$=7.0 Hz, $J_2$=9.3 Hz, 1H), 2.24 (s, 3H), 1.93 (dd, $J_1$=7.0 Hz, $J_2$=10.0 Hz, 1H), 1.26 (t, J=7.2 Hz, 3H). $^{13}$C NMR (62.5 MHz, CDCl$_3$): δ165.4, 138.4, 131.3, 129.5, 129.2, 128.6, 125.2, 72.7, 63.2, 33.8, 21.4, 20.0, 14.0. IR (neat, cm$^{-1}$): 1740, 1547, 1295, 1154. HRMS (ESI) ([M+H]$^+$) Calcd. for C$_{13}$H$_{16}$NO$_4$: 250.1079, Found 250.1081. HPLC analysis: ee=88%. OD-H (95% hexanes: 5% isopropanol, 1.0 mL/min) [Z]-isomer: $t_{major}$=5.6 min, $t_{minor}$=6.6 min.

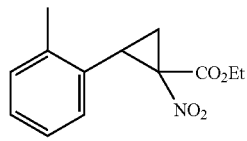

Ethyl 1-nitro-2-o-tolylcyclopropanecarboxylate: [Z]-: [α]$^{20}_D$=−14.3. (c=0.54, CHCl$_3$). $^1$H NMR (250 MHz, CDCl$_3$): δ 7.19-6.99 (m, 4H), 4.30 (q, J=7.0 Hz, 2H), 3.38 (t, J=9.8 Hz, 1H), 2.71 (dd, $J_1$=7.0 Hz, $J_2$=9.5 Hz, 1H), 2.31 (s, 3H), 1.92 (dd, $J_1$=7.0 Hz, $J_2$=10.0 Hz, 1H), 1.28 (t, J=7.2 Hz, 3H). $^{13}$C NMR (62.5 MHz, CDCl$_3$): δ 165.4, 139.1, 130.3, 129.6, 128.8, 127.3, 126.0, 71.9, 63.2, 32.7, 19.5, 19.4, 14.0. IR (neat, cm$^{-1}$): 1726, 1539, 1300, 1160. HRMS (ESI) ([M+H]$^+$) Calcd. for C$_{13}$H$_{16}$NO$_4$: 250.1079, Found 250.1085. HPLC analysis: ee=89%. OD-H (95% hexanes: 5% isopropanol, 1.0 mL/min) [Z]-isomer: $t_{major}$=6.4 min, $t_{minor}$=7.2 min.

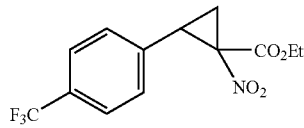

Ethyl 1-nitro-2-(4-(trifluoromethyl)phenyl)cyclopropanecarboxylate: [Z]-: [α]$^{20}_D$=−43.9. (c=1.24, CHCl$_3$). $^1$H NMR (250 MHz, CDCl$_3$): δ 7.52-7.25 (m, 4H), 4.35-4.24 (m, 2H), 3.43 (t, J=9.5 Hz, 1H), 2.61 (dd, $J_1$=7.0 Hz, $J_2$=9.3 Hz, 1H), 2.00 (dd, $J_1$=7.3 Hz, $J_2$=10.0 Hz, 1H), 1.27 (t, J=7.0 Hz, 3H). $^{13}$C NMR (62.5 MHz, CDCl$_3$): δ 164.9, 135.6, 130.5, 128.8, 125.7, 121.8, 72.6, 63.5, 32.8, 20.0, 14.0. IR (neat, cm$^{-1}$): 1744, 1549, 1326, 1127. HRMS (ESI) ([M+H]$^+$) Calcd. for C$_{13}$H$_{13}$F$_3$NO$_4$: 304.0797, Found 304.0794. HPLC analysis: ee=89%. OD-H (95% hexanes: 5% isopropanol, 1.0 mL/min) [Z]-isomer: $t_{major}$=7.3 min, $t_{minor}$=8.1 min.

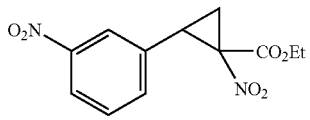

Ethyl 1-nitro-2-(3-nitrophenyl)cyclopropane-carboxylate: [Z]-: [α]$^{20}_D$=−57.5. (c=0.48, CHCl$_3$). $^1$H NMR (250 MHz, CDCl$_3$): δ 8.13-8.06 (m, 2H), 7.52-7.41 (m, 2H), 4.36-4.26 (m, 2H), 3.48 (t, J=9.3 Hz, 1H), 2.66 (dd, $J_1$=7.3 Hz, $J_2$=9.0 Hz, 1H), 2.05 (s, 3H), 1.93 (dd, $J_1$=7.3 Hz, $J_2$=9.7 Hz, 1H), 1.29 (t, J=7.0 Hz, 3H). $^{13}$C NMR (62.5 MHz, CDCl$_3$): δ 164.7, 148.3, 134.5, 133.7, 129.8, 123.7, 123.7, 72.4, 63.7, 32.4, 19.9, 14.0. IR (neat, cm$^{-1}$): 1729, 1540, 1348, 1145. HRMS (ESI) ([M+H]$^+$) Calcd. for C$_{12}$H$_{13}$N$_2$O$_6$: 281.0774, Found 281.0771. HPLC analysis: ee=94%. OD-H (95% hexanes: 5% isopropanol, 1.0 mL/min) [Z]-isomer: $t_{major}$=16.5 min, $t_{minor}$=20.2 min.

X-Ray data for [Z]-Ethyl 1-nitro-2-(3-nitrophenyl)cyclopropanecarboxylate: The X-ray intensities were measured using Bruker-APEX2 area-detector CCD diffractometer (CuKa, λ=1.54178 Å). Indexing was performed using APEX2. Frames were integrated with SAINT V7.51A software package. Absorption correction was performed by multi-scan method implemented in SADABS. The structure was solved using SHELXS-97 and refined using SHELXL-97 contained in SHELXTL v6.10 and WinGX v1.70.01 programs packages. The X-ray Crystal data and refinement conditions are shown in Table S3.

TABLE S3

Crystal data and structure refinement for [Z]-Ethyl 1-nitro-2-(3-nitrophenyl)-cyclopropanecarboxylate.

| | |
|---|---|
| Empirical formula | C$_{12}$H$_{12}$N$_2$O$_6$ |
| Formula weight | 280.24 |
| Temperature | 296(2) K |
| Wavelength | 1.54178 Å |
| Crystal system | Monoclinic |
| Space group | P2(1) |
| Unit cell dimensions | a = 7.493(2) Å, α = 90.00; |
| | b = 9.953(3) Å, β = 105.544; |
| | c = 8.579(2) Å, γ = 90.00 |
| Volume | 616.4(3) Å$^3$ |
| Z | 2 |
| Density (calculated) | 1.510 Mg/m$^3$ |
| Absorption coefficient | 1.057 mm$^{-1}$ |
| F(000) | 292 |

TABLE S3-continued

Crystal data and structure refinement for [Z]-Ethyl 1-nitro-2-(3-nitrophenyl)-cyclopropanecarboxylate.

| | |
|---|---|
| Crystal size | 0.23 × 0.20 × 0.18 mm$^3$ |
| Theta range for data collection | 5.35 to 66.54° |
| Index ranges | −8 <= h <= 8, −11 <= k <= 11, −10 <= l <= 10 |
| Reflections collected | 5151 |
| Independent reflections | 2063 [R(int) = 0.0398] |
| Completeness to theta = 66.54 | 97.1% |
| Absorption correction | None |
| Max. and min. transmission | 0.8326 and 0.7931 |
| Refinement method | Full-matrix least-squares on F$^2$ |
| Data/restraints/parameters | 2063/1/183 |
| Goodness-of-fit on F$^2$ | 1.064 |
| Final R indices [I > 2sigma(I)] | R1 = 0.0311, wR2 = 0.0789 |
| R indices (all data) | R1 = 0.0320, wR2 = 0.0794 |
| Absolute structure parameter | 0.30(19) |
| Extinction coefficient | 0.0176(15) |
| Largest diff, peak and hole | 0.145 and −0.154 e$^{-3}$ |

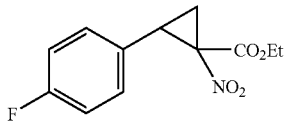

Ethyl 2-(4-fluorophenyl)-1-nitrocyclopropanecarboxylate: [Z]-: $[\alpha]^{20}_D$=−50.2. (c=0.72, CHCl$_3$). $^1$H NMR (250 MHz, CDCl$_3$): δ 7.19-7.11 (m, 2H), 6.97-6.90 (m, 2H), 4.33-4.24 (m, 2H), 3.37 (t, J=9.5 Hz, 1H), 2.56 (dd, $J_1$=7.0 Hz, $J_2$=9.3 Hz, 1H), 1.95 (dd, $J_1$=7.0 Hz, $J_2$=9.7 Hz, 1H), 1.27 (t, J=7.2 Hz, 3H). $^{13}$C NMR (62.5 MHz, CDCl$_3$): δ 165.2, 130.2, 127.2, 115.8, 100.0, 72.5, 63.3, 32.9, 20.1, 14.0. IR (neat, cm$^{-1}$): 1740, 1546, 1294, 1159. HRMS (ESI) ([M+H]$^+$) Calcd. for C$_{12}$H$_{14}$FNO$_4$: 254.0829, Found 254.0827. HPLC analysis: ee=88%. OD-H (95% hexanes: 5% isopropanol, 1.0 mL/min) [Z] isomer: $t_{major}$=6.8 min, $t_{minor}$=7.4 min.

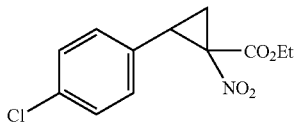

Ethyl 2-(4-chlorophenyl)-1-nitrocyclopropanecarboxylate: [Z]-: $[\alpha]^{20}_D$=−60.6. (c=1.20, CHCl$_3$). $^1$H NMR (250 MHz, CDCl$_3$): δ 7.23-7.07 (m, 4H), 4.33-4.23 (m, 2H), 3.36 (t, J=9.5 Hz, 1H), 2.56 (dd, $J_1$=7.0 Hz, $J_2$=9.0 Hz, 1H), 1.96 (dd, $J_1$=7.0 Hz, $J_2$=9.7 Hz, 1H), 1.27 (t, J=7.0 Hz, 3H). $^{13}$C NMR (62.5 MHz, CDCl$_3$): δ 165.1, 130.0, 129.7, 129.0, 72.5, 63.4, 32.4, 20.0, 14.0. IR (neat, cm$^{-1}$): 1741, 1546, 1291, 1153. HRMS (ESI) ([M+H]$^+$) Calcd. for C$_{12}$H$_{14}$ClNO$_4$: 270.0533, Found 270.0529. HPLC analysis: ee=88%. OD-H (95% hexanes: 5% isopropanol, 1.0 mL/min) [Z]-isomer: $t_{major}$=7.2 min, $t_{minor}$=7.9 min.

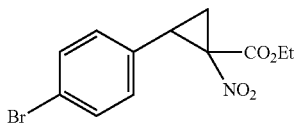

Ethyl 2-(4-bromophenyl)-1-nitrocyclopropanecarboxylate: [Z]-: $[\alpha]^{20}_D$=−54.5. (c=0.75, CHCl$_3$). $^1$H NMR (250 MHz, CDCl$_3$): δ 7.37 (d, J=7.2 Hz, 2H), 7.02 (d, J=7.2 Hz, 2H), 4.33-4.24 (m, 2H), 3.34 (t, J=9.5 Hz, 1H), 2.55 (dd, $J_1$=7.0 Hz, $J_2$=9.3 Hz, 1H), 1.96 (dd, $J_1$=7.0 Hz, $J_2$=9.7 Hz, 1H), 1.27 (t, J=7.2 Hz, 3H). $^{13}$C NMR (62.5 MHz, CDCl$_3$): δ 165.1, 131.9, 129.7, 130.5, 130.0, 122.9, 72.4, 63.4, 32.9, 20.0, 14.0. IR (neat, cm$^{-1}$): 1740, 1547, 1292, 1156. HRMS (ESI) ([M+H]$^+$) Calcd. for C$_{12}$H$_{13}$BrNO$_4$: 314.0028, Found 314.0026. HPLC analysis: ee=87%. OD-H (95% hexanes: 5% isopropanol, 1.0 mL/min) [Z]-isomer: $t_{major}$=7.7 min, $t_{minor}$=8.6 min.

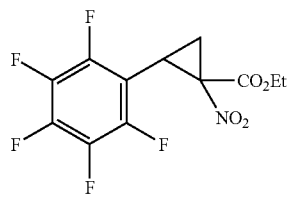

Ethyl 1-nitro-2-(perfluorophenyl)cyclopropanecarboxylate: [Z]-: $[\alpha]^{20}_D$=−43.6. (c=0.29, CHCl$_3$). $^1$H NMR (250 MHz, CDCl$_3$): δ 4.37-4.28 (m, 2H), 3.17 (t, J=9.5 Hz, 1H), 2.82 (dd, $J_1$=7.5 Hz, $J_2$=9.3 Hz, 1H), 2.14 (dd, $J_1$=7.3 Hz, $J_2$=10.3 Hz, 1H), 1.30 (t, J=7.0 Hz, 3H). $^{13}$C NMR (62.5 MHz, CDCl$_3$): δ 69.9, 63.8, 22.9, 20.7, 14.0. IR (neat, cm$^{-1}$): 1751, 1504, 1380, 1129, 952. HRMS (ESI) ([M+H]$^+$) Calcd. for C$_{12}$H$_9$F$_5$NO$_4$: 326.0452, Found 326.0451. HPLC analysis: ee=82%. OD-H (98% hexanes: 2% isopropanol, 1.0 mL/min) [Z]-isomer: $t_{major}$=7.6 min, $t_{minor}$=8.2 min.

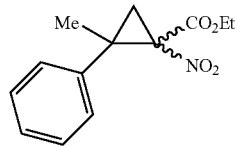

Ethyl 2-methyl-1-nitro-2-phenylcyclopropanecarboxylate: [Z]-: $^1$H NMR (250 MHz, CDCl$_3$): δ 7.23-7.209 (m, 5H), 4.30 (q, J=7.3 Hz, 2H), 2.65 (d, J=7.0 Hz, 1H), 1.867 (d, J=7.0 Hz, 1H), 1.59 (s, 3H), 1.29 (t, J=7.3 Hz, 3H). $^{13}$C NMR (62.5 MHz, CDCl$_3$): δ 164.0, 138.21, 128.7, 128.2, 127.9, 75.3, 62.9, 40.4, 26.3, 23.7, 14.1. [E]-isomer: $^1$H NMR (250 MHz, CDCl$_3$): δ 7.28-7.19 (m, 5H), 3.87-3.78 (m, 2H), 2.34 (d, J=6.7 Hz, 1H), 2.07 (d, J=6.7 Hz, 1H), 1.45 (s, 3H), 0.79 (t, J=7.3 Hz, 3H). $^{13}$C NMR (62.5 MHz, CDCl13): δ 163.6, 139.1, 128.6, 127.8, 127.7, 76.2, 62.5, 39.2, 26.3, 25.0, 13.5. HPLC ([Z]-) analysis: ee=83%. OD-H (98% hexanes: 2% isopropanol, 1.0 mL/min) [Z]-isomer: $t_{major}$=8.2 min, $t_{minor}$=10.3 min.

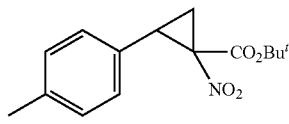

t-Butyl 1-nitro-2-p-tolylcyclopropanecarboxylate: [Z]-: $[\alpha]^{20}_D$=−49.2 (c=0.10, CHCl$_3$). $^1$H NMR (250 MHz, CDCl$_3$): δ 7.18-7.03 (m, 4H), 3.29 (t, J=9.5 Hz, 1H), 2.50 (dd, $J_1$=7.0 Hz, $J_2$=9.0 Hz, 1H), 2.33 (s, 3H), 1.84 (dd, $J_1$=7.0

Hz, J$_2$=10.0 Hz, 1H), 1.45 (s, 9H). $^{13}$C NMR (62.5 MHz, CDCl$_3$): δ 164.2, 138.3, 129.4, 128.7, 128.2, 84.7, 73.4, 32.9, 27.9, 21.2, 19.7. IR (neat, cm$^{-1}$): 1734, 1543, 1143. HRMS (ESI) ([M+NH$_4$]$^+$) Calcd. for C$_{15}$H$_{23}$N$_2$O$_4$: 295.1658, Found 295.1663. HPLC analysis: ee=92%. OJ-H (98.5% hexanes: 1.5% isopropanol, 0.8 mL/min) [Z]-isomer: t$_{major}$=14.2 min, t$_{minor}$=23.3 min.

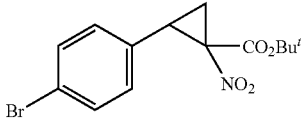

t-Butyl 2-(4-bromophenyl)-1-nitrocyclopropanecarboxylate: [Z]-: [α]$^{20}_D$=−49.5 (c=0.60, CHCl$_3$). $^1$H NMR (250 MHz, CDCl$_3$): δ 7.88-7.01 (m, 4H), 3.27 (t, J=9.5 Hz, 1H), 2.49 (dd, J$_1$=7.0 Hz, J$_2$=9.0 Hz, 1H), 1.87 (dd, J$_1$=7.0 Hz, J$_2$=10.0 Hz, 1H), 1.46 (s, 9H). $^{13}$C NMR (62.5 MHz, CDCl$_3$): δ 163.8, 131.9, 130.8, 130.0, 122.7, 85.0, 73.1, 32.2, 27.9, 19.6. IR (neat, cm$^{-1}$): 1735, 1543, 1141. HRMS (ESI) ([M+NH$_4$]$^+$) Calcd. for C$_{14}$H$_{20}$BrN$_2$O$_4$: 359.0606, Found 359.0598. HPLC analysis: ee=82%. OJ-H (98.5% hexanes: 1.5% isopropanol, 0.8 mL/min) [Z]-isomer: t$_{major}$=16.2 min, t$_{minor}$=23.4 min.

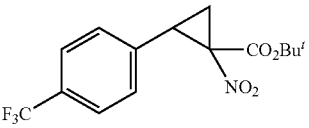

t-Butyl 1-nitro-2-(4-(trifluoromethyl)-phenyl)cyclopropanecarboxylate: [Z]-: [α]$^{20}_D$=−43.5 (c=0.75, CHCl$_3$). $^1$H NMR (250 MHz, CDCl$_3$): δ 7.50 (d, J=8.3 Hz, 2H), 7.27 (d, J=8.3 Hz, 2H), 3.35 (t, J=9.3 Hz, 1H), 2.55 (dd, J$_1$=7.3 Hz, J$_2$=9.0 Hz, 1H), 1.92 (dd, J$_1$=7.0 Hz, J$_2$=9.7 Hz, 1H), 1.47 (s, 9H). $^{13}$C NMR (62.5 MHz, CDCl$_3$): δ 163.7, 135.9, 128.8, 125.7, 125.6, 85.2, 73.2, 32.2, 27.9, 19.7. IR (neat, cm$^{-1}$): 1735, 1543, 1141. HRMS (ESI) ([M+NH$_4$]$^+$) Calcd. for C$_{15}$H$_{20}$F$_3$N$_2$O$_4$: 349.1375, Found 349.1341. HPLC analysis: ee=88%. OJ-H (98.5% hexanes: 1.5% isopropanol, 0.8 mL/min) [Z]-isomer: t$_{major}$=11.4 min, t$_{minor}$=13.0 min.

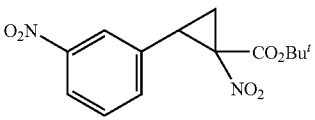

t-Butyl 1-nitro-2-(3-nitrophenyl)cyclopropanecarboxylate: [Z]-: [α]$^{20}_D$=−41.8 (c=0.31, CHCl$_3$). $^1$H NMR (250 MHz, CDCl$_3$): δ 8.13-8.06 (m, 2H), 7.51-7.41 (m, 2H), 3.40 (t, J=9.3 Hz, 1H), 2.63-2.56 (m, 1H), 2.01-1.94 (m, 1H), 1.48 (s, 9H). $^{13}$C NMR (62.5 MHz, CDCl$_3$): δ 163.4, 148.3, 134.4, 134.1, 129.7, 123.7, 123.6, 85.4, 73.1, 31.8, 27.9, 19.6. IR (neat, cm$^{-1}$): 1735, 1530, 1347, 1140. HRMS (ESI) ([M+NH$_4$]$^+$) Calcd. for C$_{14}$H$_{20}$N$_3$O$_6$: 326.1352, Found 326.1346. HPLC analysis: ee=78%. AD-H (95% hexanes: 5% isopropanol, 1.0 mL/min) [Z]-isomer: t$_{major}$=7.4 min, t$_{minor}$=8.1 min.

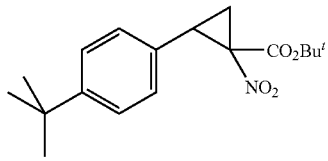

t-Butyl 2-(4-t-butylphenyl)-1-nitrocyclopropanecarboxylate: [Z]-isomer: [α]$^{20}_D$=−55.4 (c=0.98, CHCl$_3$). $^1$H NMR (250 MHz, CDCl$_3$): δ 7.26-7.05 (m, 4H), 3.29 (t, J=9.5 Hz, 1H), 2.51 (dd, J$_1$=7.0 Hz, J$_2$=9.3 Hz, 1H), 1.85 (dd, J$_1$=7.0 Hz, J$_2$=10.0 Hz, 1H), 1.46 (s, 9H), 1.21 (s, 9H). $^{13}$C NMR (62.5 MHz, CDCl$_3$): δ 164.2, 151.4, 128.7, 128.0, 125.6, 84.7, 73.4, 34.6, 32.9, 31.3, 27.9, 19.8. IR (neat, cm$^{-1}$): 1733, 1542, 1144. HRMS (ESI) ([M+Na]$^+$) Calcd. for C$_{18}$H$_{25}$NNaO$_4$: 342.1681, Found 342.1668. HPLC analysis: ee=92%. OJ-H (98.5% hexanes: 1.5% isopropanol, 0.8 mL/min) [Z]-isomer: t$_{major}$=10.0 min, t$_{minor}$=16.0 min.

General Procedures for Cyclopropanation of Aliphatic Olefin. Catalyst (5 mol %) was placed in an oven-dried, resealable Schlenk tube. The tube was capped with a Teflon screwcap, evacuated, and backfilled with nitrogen. The screwcap was replaced with a rubber septum, and 1.0 mL aliphatic olefin was added via syringe, followed by 0.25 mmol diazo compound. The tube was purged with nitrogen for 1 min and its contents were stirred at room temperature. After the reaction finished, the resulting mixture was concentrated and the residue was purified by flash silica gel chromatography to give the product.

Ethyl 2-butyl-1-nitrocyclopropanecarboxylate: [Z]- and [E]-isomers are inseparable. [E]-: $^1$H NMR (250 MHz, CDCl$_3$): δ 4.31-4.20 (m, 2H), 2.40-2.32 (m, 2H), 1.65-1.56 (m, 2H), 1.29-1.23 (m, 10H), 0.85-0.82 (m, 3H). [Z]-: $^1$H NMR (250 MHz, CDCl$_3$): δ 4.31-4.20 (m, 2H), 2.06-2.02 (m, 2H), 1.83-1.76 (m, 2H), 1.29-1.23 (m, 10H), 0.85-0.82 (m, 3H). [Z]- and [E]-mixture: $^{13}$C NMR (62.5 MHz, CDCl$_3$): δ 166.1, 163.6, 71.5, 70.6, 62.9, 62.7, 30.6, 30.4, 30.4, 29.3, 27.6, 23.2, 22.4, 22.3, 22.2, 14.0, 14.0, 13.9, 13.9. HRMS (ESI) ([M+H]$^+$) Calcd. for C$_{10}$H$_{18}$NO$_4$: 216.1236, Found 216.1215.

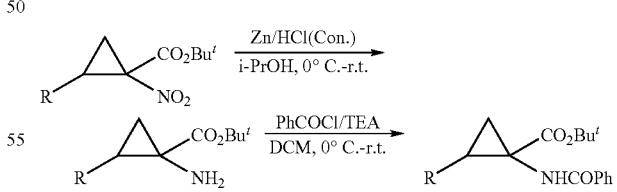

General Procedures for Reduction and Amidation of Aliphatic Nitro-Cyclopropane: (The reduction step followed the literature; Wurz R. P., Charette A. B., J. Org. Chem. 2004, 69, 1262-1269.) Cooled by ice water, Ethyl 2-butyl-1-nitrocyclopropanecarboxylate (0.10 mmol) was dissolved in 2.0 mL of i-PrOH and treated with concentrated HCl (1.1 mL, 10 equiv). Zinc dust (130 mg, 2.0 mmol, 20 equiv) was added in one portion and the solution allowed stirring for 2 h at room temperature. The suspension was quenched by addition of a saturated solution of NaHCO₃ (4 mL). The aqueous phase was extracted with dichloromethane (4 mL×3), the combined organic extracts were dried over anhydrous MgSO₄ and filtered, and concentrate the solvent to about 1.0-2.0 ml under reduced pressure. Then cooled by ice-water, to the about DCM solution, 40 μL Et₃N was added, followed by 27 μL PhCOCl, and the solution allowed to stir for 1 h at room temperature. The resulting solution was quenched by addition of water (2 drops), remove the solvent and water at 40° C. under reduced pressure. The crude residue was then chromatographed on silica gel pretreated with 1:3 EtOAc/hexanes, affording the product.

Ethyl 1-benzamido-2-butylcyclopropanecarboxylate: [E]-: $[\alpha]^{20}{}_D$=8.9 (c=0.17, CHCl₃). ¹H NMR (250 MHz, CDCl₃): δ 7.72-7.68 (m, 2H), 7.45-7.19 (m, 3H), 6.59 (s, br, 1H), 4.16-4.10 (m, 2H), 1.60-0.84 (m, 17H). ¹³C NMR (62.5 MHz, CDCl₃): δ 171.1, 168.2, 134.2, 131.7, 128.6, 127.0, 61.3, 38.6, 31.5, 31.4, 26.8, 23.0, 22.5, 14.3, 14.1. HRMS (ESI) ([M+H]⁺) Calcd. for $C_{17}H_{24}NO_3$: 290.1756, Found 290.1753. HPLC analysis: ee=15%. OD-H (95% hexanes: 5% isopropanol, 1.0 mL/min) [E]-isomer: $t_{minor}$=15.4 min, $t_{major}$=19.8 min.

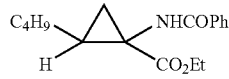

Ethyl 1-benzamido-2-butylcyclopropanecarboxylate: [Z]-: $[\alpha]^{20}{}_D$=-10.7 (c=0.375, CHCl₃). ¹H NMR (250 MHz, CDCl₃): δ 7.73-7.70 (m, 2H), 7.46-7.19 (m, 3H), 6.40 (s, br, 1H), 4.12-4.04 (m, 2H), 1.76-0.82 (m, 17H). ¹³C NMR (62.5 MHz, CDCl₃): δ 172.6, 168.9, 134.4, 131.8, 128.76, 127.0, 61.4, 37.9, 31.4, 28.4, 28.1, 23.0, 22.5, 14.2, 14.1. HRMS (ESI) ([M+H]⁺) Calcd. for $C_{17}H_{24}NO_3$: 290.1756, Found 290.1754. HPLC analysis: ee=70%. OD-H (95% hexanes: 5% isopropanol, 1.0 mL/min) [Z]-isomer: $t_{minor}$=14.3 min, $t_{major}$=17.1 min.

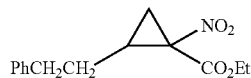

Ethyl 1-nitro-2-phenethylcyclopropanecarboxylate: [E]-: $[\alpha]^{20}{}_D$=-4.4 (c=0.19, CHCl₃). ¹H NMR (250 MHz, CDCl₃): δ 7.23-7.08 (m, 5H), 4.28-4.23 (m, 2H), 2.71-2.65 (m, 2H), 2.43-2.30 (m, 1H), 1.82-1.76 (m, 2H), 1.59-1.50 (m, 2H), 1.29-1.23 (m, 3H). ¹³C NMR (62.5 MHz, CDCl₃): δ 163.6, 140.5, 128.6, 128.4, 126.3, 70.5, 62.9, 34.7, 29.8, 23.0, 14.0. HRMS (ESI) ([M+H]⁺) Calcd. for $C_{14}H_{18}NO_4$: 264.1236, Found 264.1215. HPLC analysis: ee=14%. OD-H (95% hexanes: 5% isopropanol, 1.0 mL/min) [E]-isomer: $t_{minor}$=10.2 min, $t_{major}$=11.8 min.

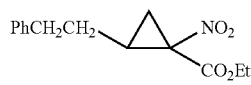

Ethyl 1-nitro-2-phenethylcyclopropanecarboxylate: [Z]-: $[\alpha]^{20}{}_D$=2.3 (c=0.385, CHCl₃). ¹H NMR (250 MHz, CDCl₃): δ 7.22-7.07 (m, 5H), 4.25-4.17 (m, 2H), 2.72-2.66 (m, 2H), 2.10-2.03 (m, 1H), 1.76-1.70 (m, 2H), 1.64-1.50 (m, 2H), 1.26-1.20 (m, 3H). ¹³C NMR (62.5 MHz, CDCl₃): δ 165.9, 140.5, 128.6, 128.5, 126.3, 71.5, 63.0, 34.4, 30.3, 28.7, 22.2, 14.0. HRMS (ESI) ([M+H]⁺) Calcd. for $C_{14}H_{18}NO_4$: 264.1236, Found 264.1197. HPLC analysis: ee=69%. OJ-H (98.5% hexanes: 1.5% isopropanol, 1.0 mL/min) [Z]-isomer: $t_{major}$=26.2 min, $t_{minor}$=33.1 min.

t-Butyl 2-butyl-1-nitrocyclopropanecarboxylate: [Z]-: ¹H NMR (250 MHz, CDCl₃): δ 2.00-1.93 (m, 1H), 1.72-1.66 (m, 1H), 1.53-1.50 (m, 2H), 1.45-1.25 (m, 14H), 0.82 (t, J=7.0 Hz, 3H). ¹³C NMR (62.5 MHz, CDCl₃): δ 164.8, 84.2, 72.2, 30.5, 28.7, 28.0, 27.9, 22.3, 22.0, 13.9. HRMS (ESI) ([M+NH₄]⁺) Calcd. for $C_{12}H_{28}N_2O_4$: 261.1814, Found 261.1771.

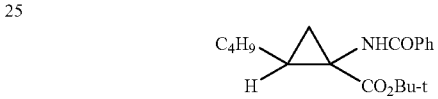

t-Butyl 1-benzamido-2-butylcyclopropanecarboxylate: [Z]-: $[\alpha]^{20}{}_D$=-10.7 (c=0.49, CHCl₃). ¹H NMR (250 MHz, CDCl₃): δ 7.72-7.69 (m, 2H), 7.44-7.33 (m, 3H), 6.38 (s, br, 1H), 1.67-1.65 (m, 3H), 1.40-1.24 (m, 14H), 0.86-0.81 (m, 4H). ¹³C NMR (62.5 MHz, CDCl₃): δ 171.6, 168.9, 134.7, 131.6, 128.6, 127.0, 81.3, 38.6, 31.5, 28.1, 28.0, 28.0, 27.8, 22.5, 14.1. HRMS (ESI) ([M+Na]⁺) Calcd. for $C_{19}H_{27}NaNO_3$: 340.1889, Found 340.1885. HPLC analysis: ee=80%. OD-H (95% hexanes: 5% isopropanol, 0.7 mL/min) [Z]-isomer: $t_{minor}$=10.9 min, $t_{major}$=16.9 min.

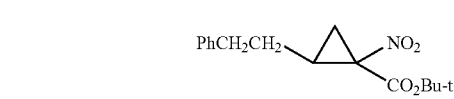

t-Butyl 1-nitro-2-phenethylcyclopropanecarboxylate: [Z]-: ¹H NMR (250 MHz, CDCl₃): δ 7.21-7.07 (m, 5H), 2.73-2.65 (m, 2H), 1.98-1.95 (m, 1H), 1.74-1.65 (m, 2H), 1.55-1.32 (m, 11H). ¹³C NMR (62.5 MHz, CDCl₃): δ 164.7, 140.6, 128.5, 128.5, 126.3, 84.45, 72.1, 34.5, 30.3, 28.0, 27.9, 21.8. HRMS (ESI) ([M+NH4]⁺) Calcd. for $C_{18}H_{28}N_2O_4$: 309.1814, Found 309.1778.

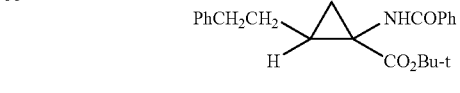

t-Butyl 1-benzamido-2-phenethylcyclopropanecarboxylate: [Z]-: $[\alpha]^{20}{}_D$=21.8 (c=0.90, CHCl₃). ¹H NMR (250 MHz, CDCl₃): δ 7.45-7.11 (m, 10H), 5.49 (s, br, 1H), 2.82-2.61 (m, 2H), 1.97-1.86 (m, 1H), 1.70-1.61 (m, 3H), 1.97-1.86 (m, 1H), 1.34 (s, 9H), 0.86-0.84 (m, 1H). ¹³C NMR (62.5 MHz, CDCl₃): δ 171.4, 169.0, 141.8, 134.6, 131.5, 128.9, 128.7, 128.4, 127.0, 126.2, 81.2, 38.6, 35.8, 30.5, 28.0, 27.6, 22.3. HRMS (ESI) ([M+H]⁺) Calcd. for $C_{23}H_{28}NO_3$: 366.2069, Found 366.2074. HPLC analysis: ee=86%. AD-H (98% hexanes: 2% isopropanol, 1.0 mL/min) [Z]-isomer: $t_{minor}$=48.6 min, $t_{major}$=52.3 min.

General Procedures for Cyclopropanation of Electron Deficient Olefin: Catalyst (5 mol %) was placed in an oven-dried, resealable Schlenk tube. The tube was capped with a Teflon screwcap, evacuated, and backfilled with nitrogen. The screwcap was replaced with a rubber septum, and 1.25 mmol olefin (dissolve in 1.0 mL PhCl) was added via syringe, followed by 0.25 mmol diazo compound. The tube was purged with nitrogen for 1 min and its contents were stirred at room temperature. After the reaction finished, the resulting mixture was concentrated and the residue was purified by flash silica gel chromatography to give the product. The [Z], [E]-isomers can be separated by column.

1-Ethyl 2-methyl 1-nitrocyclopropane-1,2-dicarboxylate: [E]-: $[\alpha]^{20}_D$=7.0 (c=0.115, CHCl$_3$). $^1$H NMR (250 MHz, CDCl$_3$): δ 4.27 (q, J=7.3 Hz, 2H), 3.69 (s, 3H), 3.11-3.03 (m, 1H), 2.17-2.11 (m, 1H), 1.28 (t, J=7.3 Hz, 3H). $^{13}$C NMR (62.5 MHz, CDCl$_3$): δ 167.7, 160.7, 63.3, 53.0, 29.6, 21.0, 13.8. HRMS (ESI) ([M+H]$^+$) Calcd. for C$_8$H$_{12}$NO$_6$: 218.0665, Found 218.0655. HPLC analysis: ee=29%. Whelk-O1 (98.5% hexanes: 1.5% isopropanol, 1.0 mL/min) [E]-isomer: $t_{minor}$=12.7 min, $t_{major}$=15.5 min.

1-Ethyl 2-methyl 1-nitrocyclopropane-1,2-dicarboxylate: [Z]-: $[\alpha]^{20}_D$=-40.8 (c=0.155, CHCl$_3$). $^1$H NMR (250 MHz, CDCl$_3$): δ 4.31-4.21 (m, 2H), 3.69 (s, 3H), 2.83-2.70 (m, 1H), 2.45-2.39 (m, 1H), 1.98-1.90 (m, 1H), 1.29-1.22 (m, 3H). $^{13}$C NMR (62.5 MHz, CDCl$_3$): δ 167.3, 164.2, 64.0, 53.2, 29.2, 21.1, 13.9. HRMS (ESI) Calcd. for C$_8$H$_{12}$NO$_6$: 218.0665, Found 218.0649. HPLC analysis: ee=80%. Whelk-O1 (98.5% hexanes: 1.5% isopropanol, 1.0 mL/min) [Z]-isomer: $t_{minor}$=17.4 min, $t_{major}$=20.2 min.

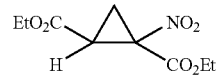

1-Ethyl 2-ethyl 1-nitrocyclopropane-1,2-dicarboxylate: [Z]-: $[\alpha]^{20}_D$=-72.9 (c=0.45, CHCl$_3$). $^1$H NMR (250 MHz, CDCl$_3$): δ 4.29-4.09 (m, 4H), 2.78 (dd, J$_1$=8.3 Hz, J$_2$=9.0 Hz, 1H), 2.41 (dd, J$_1$=6.5 Hz, J$_2$=7.8 Hz, 1H), 1.92 (dd, J$_1$=6.3 Hz, J$_2$=9.3 Hz, 1H), 1.18-1.28 (m, 6H). $^{13}$C NMR (62.5 MHz, CDCl$_3$): δ 166.7, 164.3, 71.1, 63.9, 62.4, 29.4, 21.0, 14.0, 13.9. HPLC analysis: ee=88%. OJ-H (99.3% hexanes: 0.7% isopropanol, 0.7 mL/min) [Z]-isomer: $t_{minor}$=43.7 min, $t_{major}$=51.8 min.

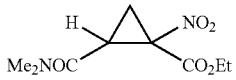

Ethyl 2-(dimethylcarbamoyl)-1-nitrocyclopropanecarboxylate: [Z]/[E] mixture ([Z]/[E]=63/37): $[\alpha]^{20}_D$=-1.65 (c=0.85, CHCl$_3$). inseparable [Z]/[E] mixture: $^1$H NMR (250 MHz, CDCl$_3$): [E]-: δ 4.30-4.20 (m, 2H), 3.24-3.12 (m, 1H), 3.11 (s, 3H), 2.90 (s, 3H), 2.33-2.27 (m, 1H), 2.07-2.00 (m, 1H), 1.28-1.20 (m, 3H). [Z]-: δ 4.30-4.20 (m, 2H), 3.11 (s, 3H), 3.00-2.91 (m, 1H), 2.90 (s, 3H), 2.62-2.56 (m, 1H), 1.84-1.78 (m, 1H), 1.28-1.20 (m, 3H). $^{13}$C NMR (62.5 MHz, CDCl$_3$): [Z] and [E] mixture: δ 164.9, 164.8, 164.5, 161.4, 70.9, 70.6, 63.8, 63.0, 37.4, 37.4, 36.2, 35.9, 29.4, 228.7, 20.6, 20.3, 13.9, 13.8. HPLC analysis: ee ([E])=22%. Whelk-O1 (95% hexanes: 5.0% isopropanol, 1.0 mL/min) [E]-isomer: $t_{major}$=44.8, min, $t_{minor}$=58.0 min; [Z]-isomer: $t_{minor}$=66.9 min, $t_{major}$=106.5 min.

The foregoing non-limiting examples are provided to illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

What is claimed is:

1. A method for cyclopropanation of an olefin, the process comprising treating an olefin with an electron acceptor substituted nitro diazo reagent in the presence of a chiral cobalt (II) porphyrin complex with D$_2$-symmetry.

2. The method of claim 1 wherein the olefin corresponds to Formula 1

Formula 1 wherein R$_1$, R$_2$, R$_3$, and R$_4$ are independently hydrogen, hydrocarbyl, substituted hydrocarbyl, heterocyclo, or an electron withdrawing group.

3. The method of claim 1 wherein the olefin is styrene, substituted styrene, an α,β-unsaturated ester, or an α,β-unsaturated ketone.

4. The method of claim 2 wherein at least one of R$_1$, R$_2$, R$_3$, and R$_4$ is selected from the group consisting of phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, and dimethylcarbamoyl.

5. The method of claim 2 wherein the diazo reagent corresponds to Formula 7

Formula 7 wherein R$_{10}$ is an electron acceptor.

6. The method of claim 5 wherein R$_{10}$ is selected from the group consisting of an aldehyde, a ketone, an ester, and a carboxylic acid.

7. The method of claim 2 wherein the diazo reagent corresponds to Formula 8

Formula 8 wherein $R_{11}$ is hydrogen, hydrocarbyl, substituted hydrocarbyl, heterocyclo, halogen, —$OR_{20}$, —$NR^aR^b$, or —$OC(O)R_{21}$, wherein $R_{20}$ is hydrogen, hydrocarbyl, substituted hydrocarbyl, or heterocyclo; $R^a$ and $R^b$ are independently hydrogen, hydrocarbyl, substituted hydrocarbyl or heterocyclo; and $R_{21}$ is hydrocarbyl, substituted hydrocarbyl or heterocyclo.

8. The method of claim 2 wherein the diazo reagent corresponds to Formula 9

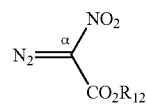

Formula 9 wherein $R_{12}$ is hydrogen, hydrocarbyl, substituted hydrocarbyl, or heterocyclo.

9. The method of claim 8 wherein $R_{12}$ is selected from the group consisting of ethyl, methyl, butyl, or propyl.

10. The method of claim 9 wherein at least one of $R_1$, $R_2$, $R_3$, and $R_4$ is selected from the group consisting of phenyl, t-butylphenyl, tolyl, trifluoromethyl phenyl, nitrophenyl, fluorophenyl, chlorophenyl, bromophenyl, perfluorophenyl, butyl, phenyethyl, methyl carboxylate, ethyl carboxylate, and dimethylcarbamoyl.

11. The method of claim 1 wherein the method yields a nitro-substituted cyclopropane corresponding to Formula Z

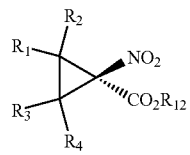

Formula Z wherein $R_1$, $R_2$, $R_3$, and $R_4$ are independently hydrogen, hydrocarbyl, substituted hydrocarbyl, heterocyclo, or an electron withdrawing group; and $R_{12}$ is hydrogen, hydrocarbyl, substituted hydrocarbyl, or heterocyclo.

12. The method of claim 1 wherein the chiral cobalt(II) porphyrin complex with $D_2$-symmetry is selected from the group consisting of

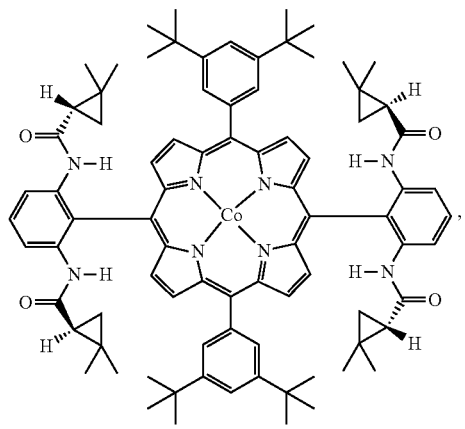

[Co(P1)]

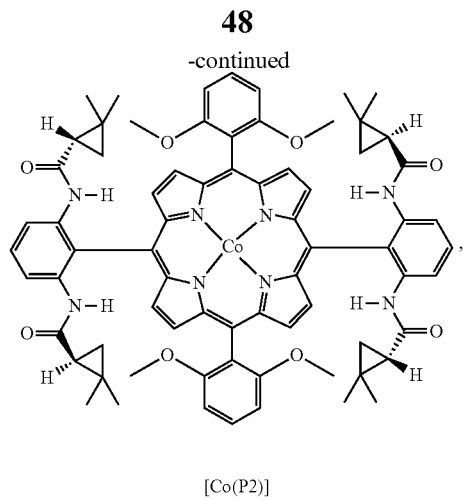

[Co(P2)]

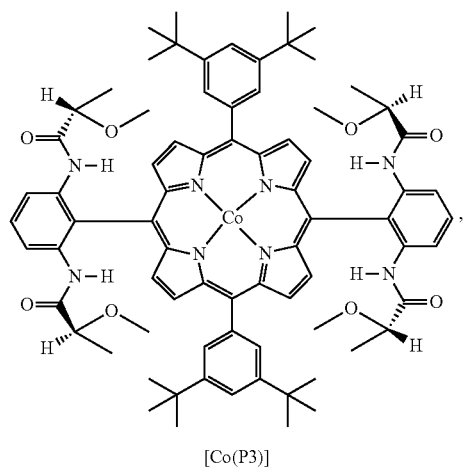

[Co(P3)]

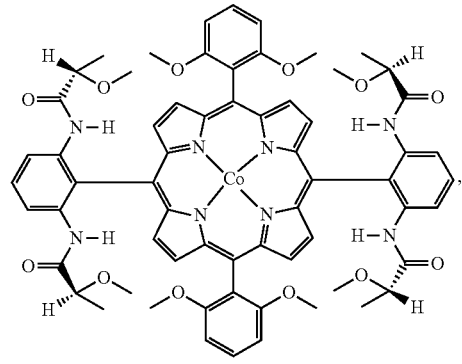

[Co(P4)]

-continued
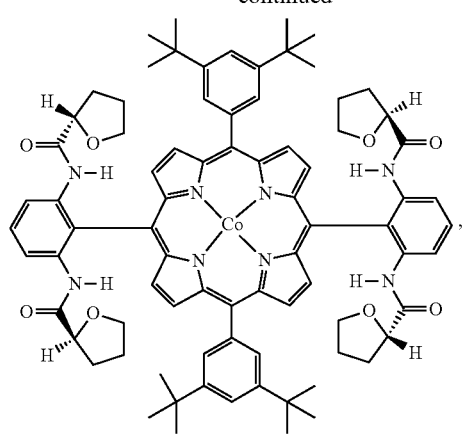
[Co(P5)]
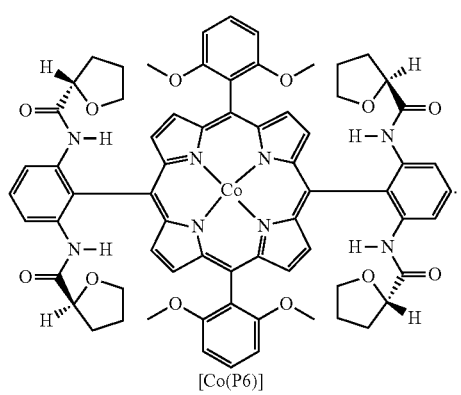
[Co(P6)]
13. The method of claim 2 wherein the chiral cobalt(II) porphyrin complex with $D_2$-symmetry is selected from the group consisting of
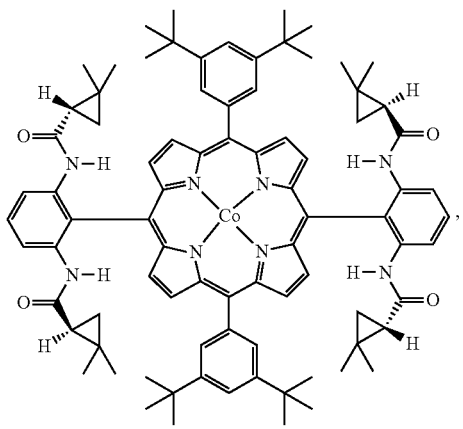
[Co(P1)]
-continued
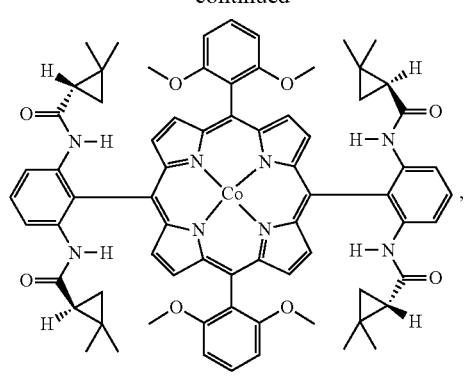
[Co(P2)]
and
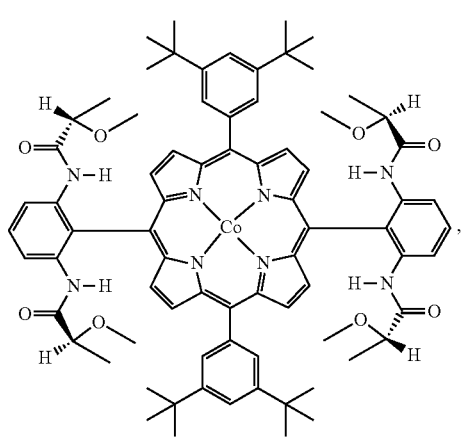
[Co(P3)]
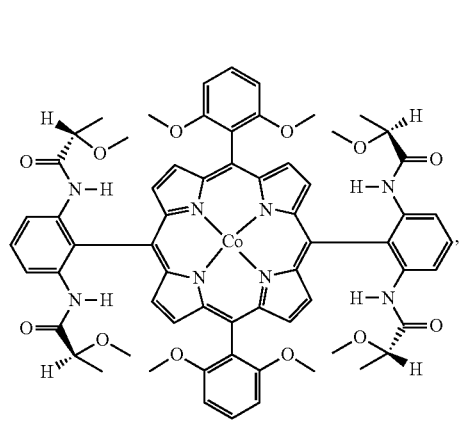
[Co(P4)]

-continued
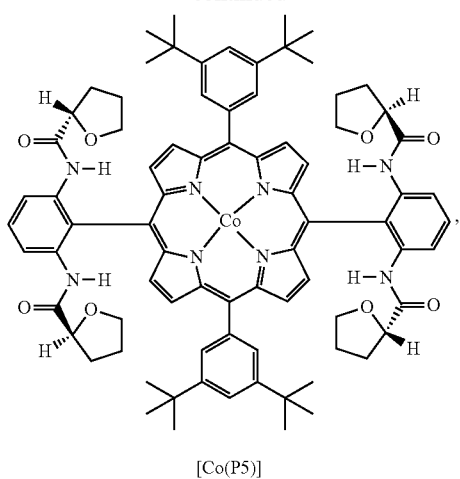
[Co(P5)]
and
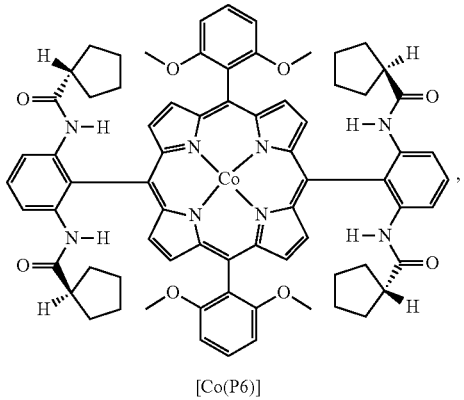
[Co(P6)]
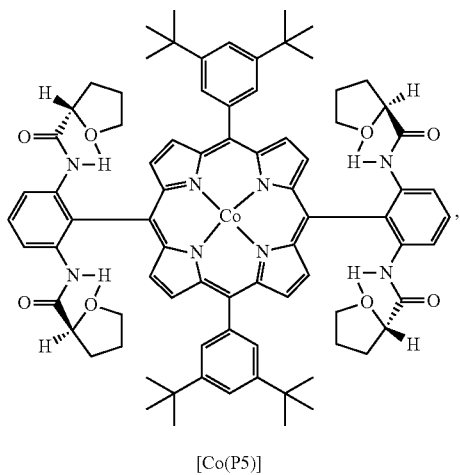
[Co(P5)]
and
-continued
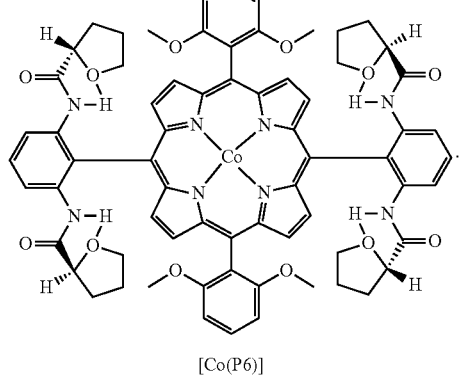
[Co(P6)]
14. The method of claim 3 wherein the chiral cobalt(II) porphyrin complex with $D_2$-symmetry is selected from the group consisting of
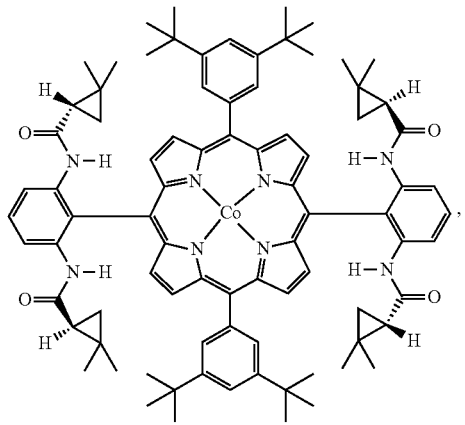
[Co(P1)]
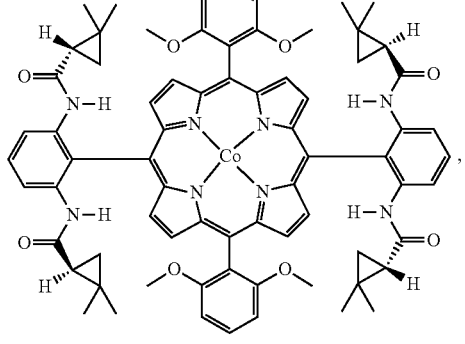
[Co(P2)]

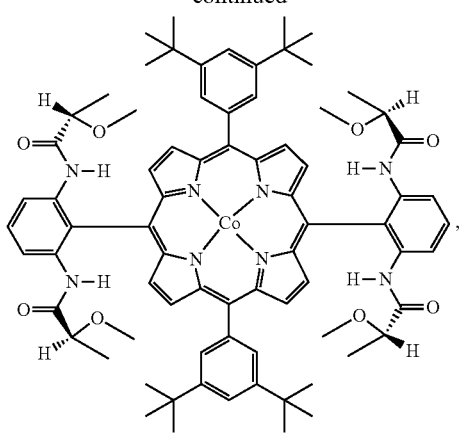
[Co(P3)]
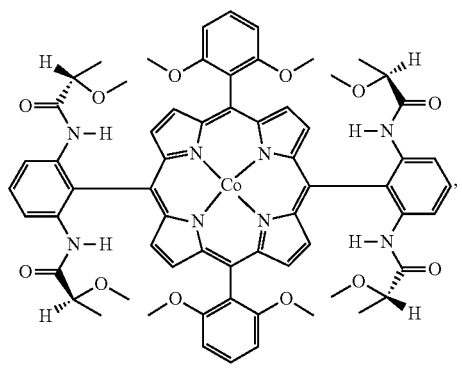
[Co(P4)]
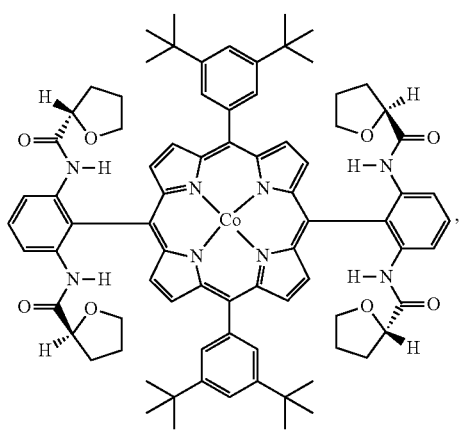
[Co(P5)]
and
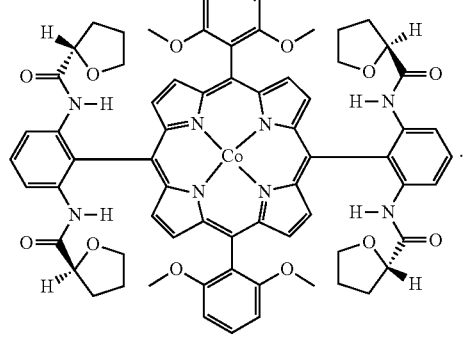
[Co(P6)]
15. The method of claim 5 wherein the chiral cobalt(II) porphyrin complex with $D_2$-symmetry is selected from the group consisting of
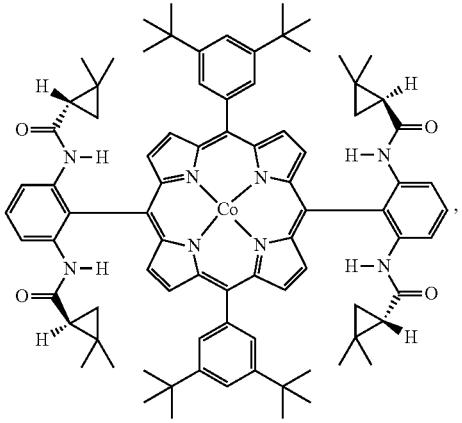
[Co(P1)]
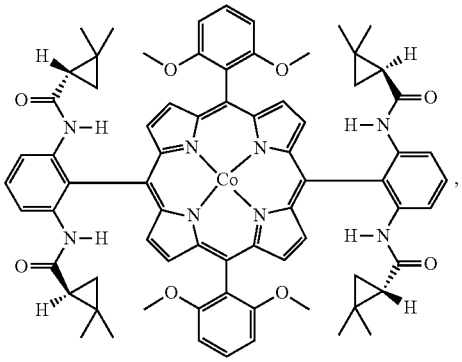
[Co(P2)]

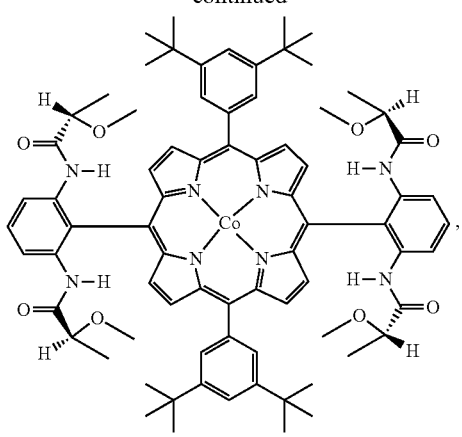
[Co(P3)]
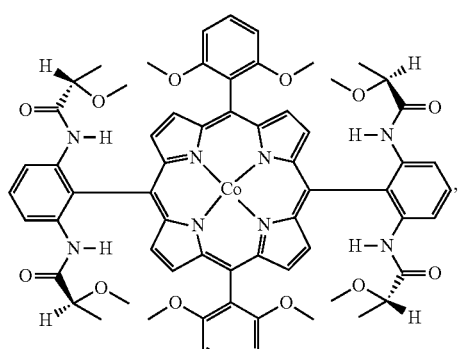
[Co(P4)]
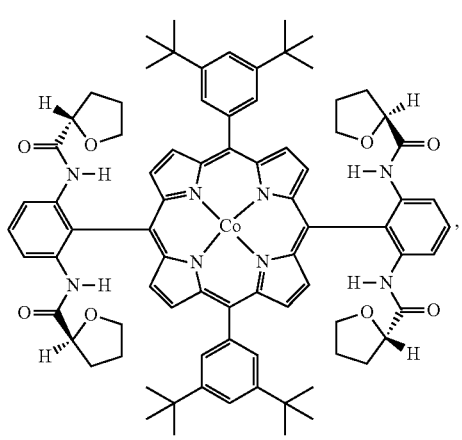
[Co(P5)]
and
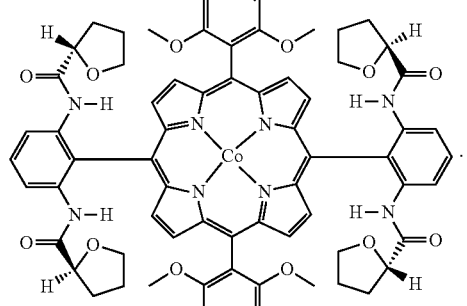
[Co(P6)]
16. The method of claim 7 wherein the chiral cobalt(II) porphyrin complex with $D_2$-symmetry is selected from the group consisting of
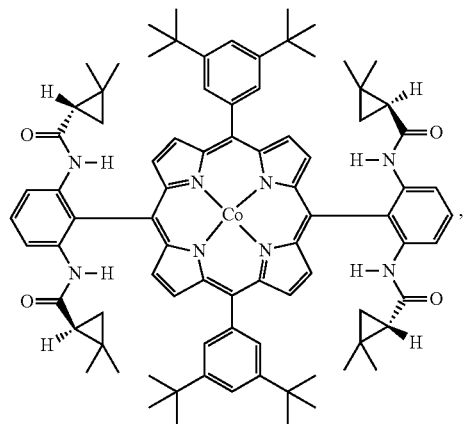
[Co(P1)]
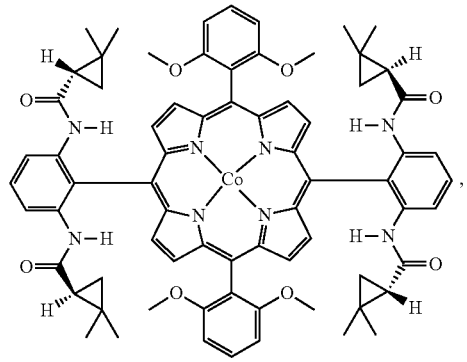
[Co(P2)]

-continued
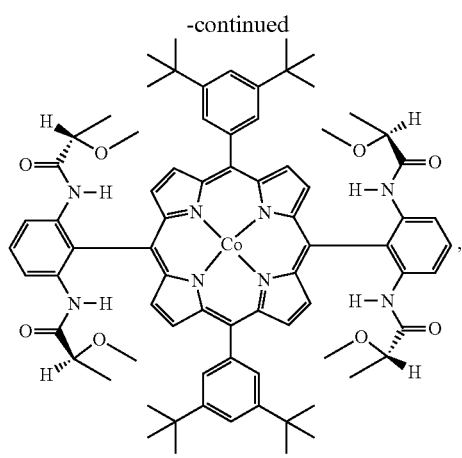
[Co(P3)]
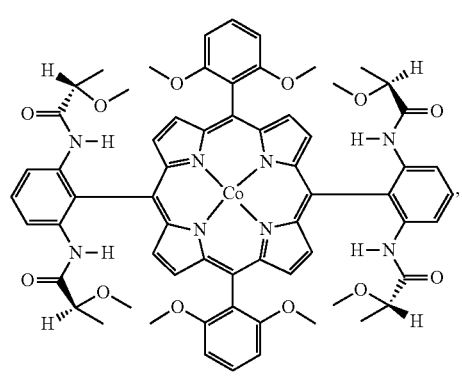
[Co(P4)]
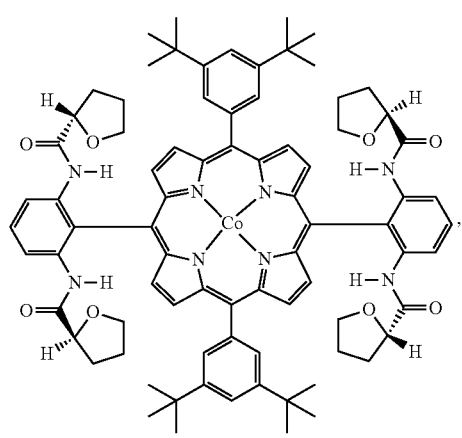
[Co(P5)]
and
-continued
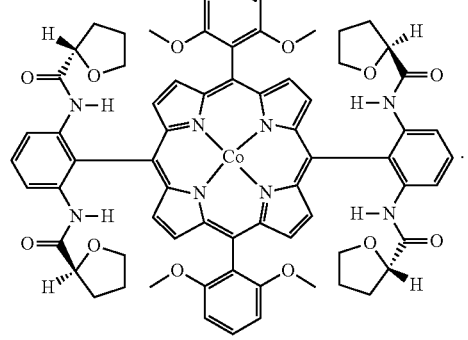
[Co(P6)]
17. The method of claim 8 wherein the chiral cobalt(II) porphyrin complex with $D_2$-symmetry is selected from the group consisting of
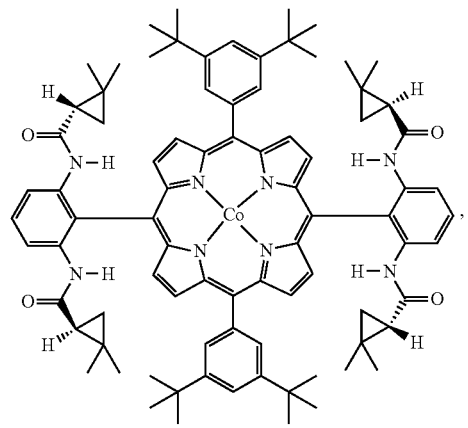
[Co(P1)]
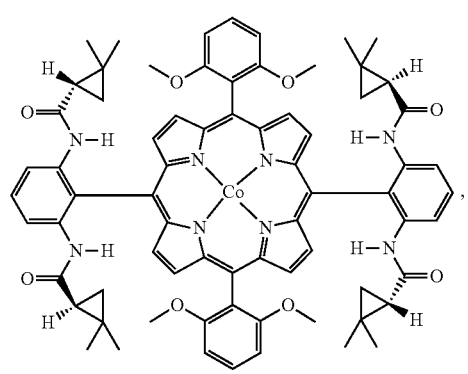
[Co(P2)]

-continued

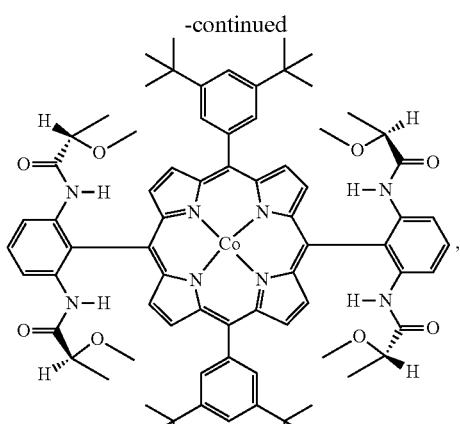

[Co(P3)]

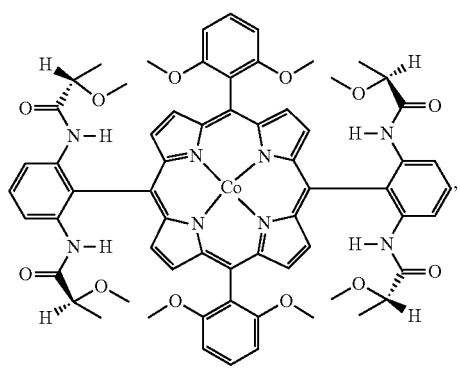

[Co(P4)]

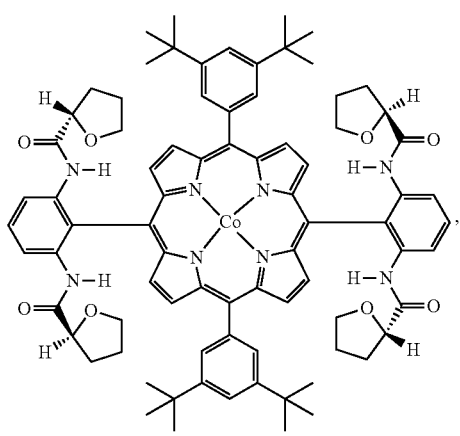

[Co(P5)]

and

-continued

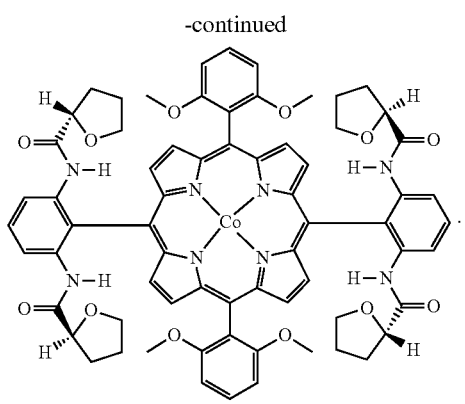

[Co(P6)]

18. The method of claim 1 wherein the diazo reagent corresponds to Formula 7

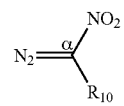

Formula 7 wherein $R_{10}$ is an electron acceptor.

19. The method of claim 18 wherein $R_{10}$ is selected from the group consisting of an aldehyde, a ketone, an ester, and a carboxylic acid.

20. The method of claim 1 wherein the diazo reagent corresponds to Formula 8

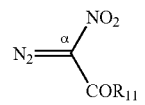

Formula 8 wherein $R_{11}$ is hydrogen, hydrocarbyl, substituted hydrocarbyl, heterocyclo, halogen, —$OR_{20}$, —$NR^{a}R^{b}$, or —$OC(O)R_{21}$, wherein $R_{20}$ is hydrogen, hydrocarbyl, substituted hydrocarbyl, or heterocyclo; $R^{a}$ and $R^{b}$ are independently hydrogen, hydrocarbyl, substituted hydrocarbyl or heterocyclo; and $R_{21}$ is hydrocarbyl, substituted hydrocarbyl or heterocyclo.

21. The method of claim 1 wherein the diazo reagent corresponds to Formula 9

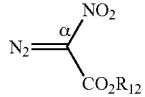

Formula 9 wherein $R_{12}$ is hydrogen, hydrocarbyl, substituted hydrocarbyl, or heterocyclo.

22. The method of claim 21 wherein $R_{12}$ is selected from the group consisting of ethyl, methyl, butyl, or propyl.

23. The method of claim 1 wherein the method yields a nitro-substituted cyclopropane corresponding to Formula Z

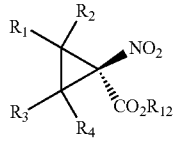

Formula Z wherein $R_1$, $R_2$, $R_3$, and $R_4$ are independently hydrogen, hydrocarbyl, substituted hydrocarbyl, heterocyclo, or an electron withdrawing group; and $R_{12}$ is hydrogen, hydrocarbyl, substituted hydrocarbyl, or heterocyclo.

24. The method of claim 1 wherein the chiral cobalt(II) porphyrin complex with $D_2$-symmetry corresponds to Formula [Co(P1)]:

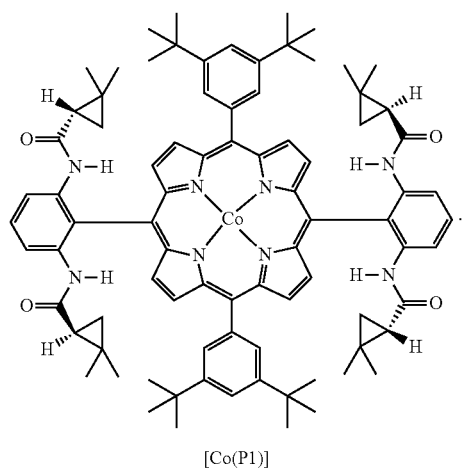

[Co(P1)]

25. The method of claim 18 wherein the chiral cobalt(II) porphyrin complex with $D_2$-symmetry corresponds to Formula [Co(P1)]:

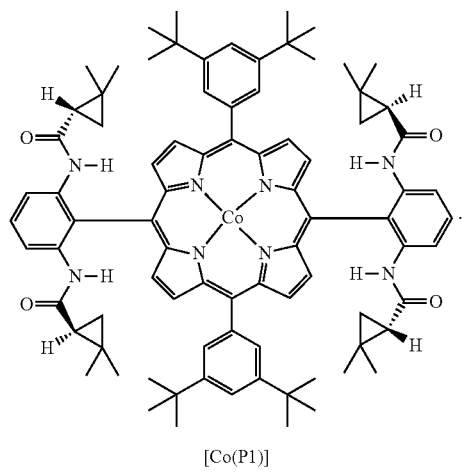

[Co(P1)]

26. The method of claim 19 wherein the chiral cobalt(II) porphyrin complex with $D_2$-symmetry corresponds to Formula [Co(P1)]:

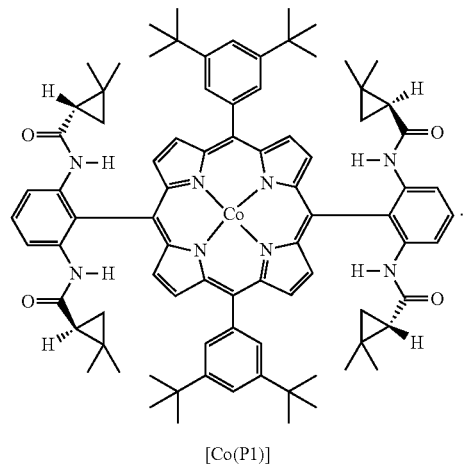

[Co(P1)]

27. The method of claim 20 wherein the chiral cobalt(II) porphyrin complex with $D_2$-symmetry corresponds to Formula [Co(P1)]:

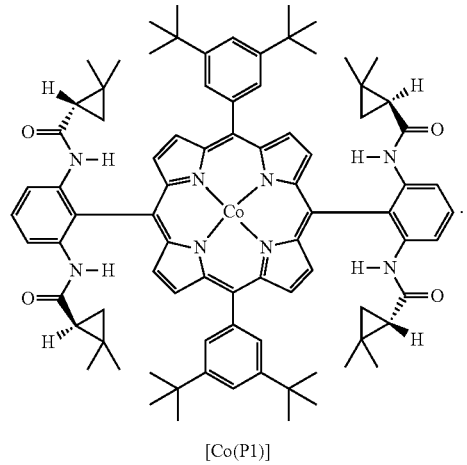

[Co(P1)]

28. The method of claim 21 wherein the chiral cobalt(II) porphyrin complex with $D_2$-symmetry corresponds to Formula [Co(P1)]:

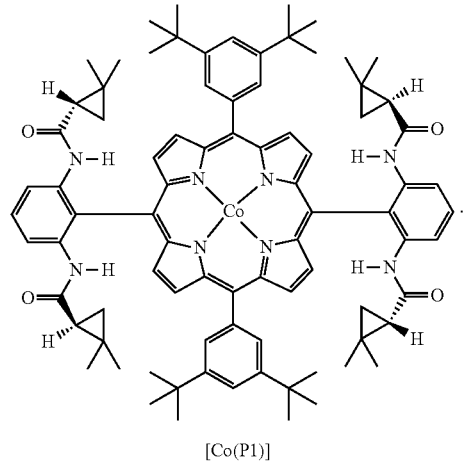

[Co(P1)]

29. The method of claim 22 wherein the chiral cobalt(II) porphyrin complex with $D_2$-symmetry corresponds to Formula [Co(P1)]:

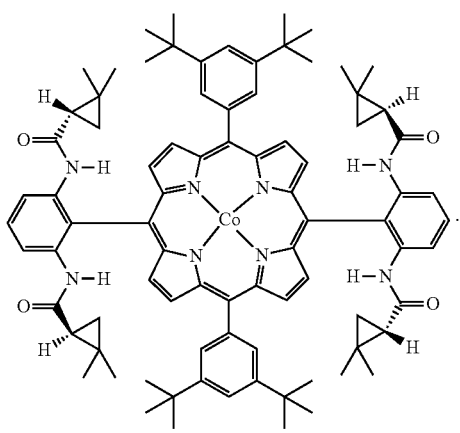
[Co(P1)]
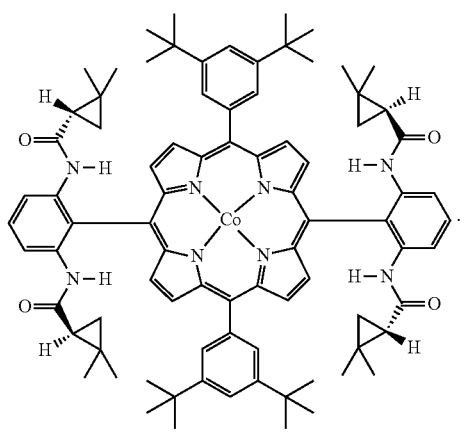
[Co(P1)]
30. The method of claim 23 wherein the chiral cobalt(II) porphyrin complex with $D_2$-symmetry corresponds to Formula [Co(P1)]:
* * * * *